US012564546B2

(12) United States Patent
Cordeiro et al.

(10) Patent No.: US 12,564,546 B2
(45) **Date of Patent: *Mar. 3, 2026**

(54) SELF-TANNING COMPOSITIONS CONTAINING AN AROMATIC SULFONATE AND METHODS THEREOF

(71) Applicant: Kao Corporation, Tokyo (JP)

(72) Inventors: Jordan Cordeiro, Erlanger, KY (US); Emily Meiser, Cincinnati, OH (US); Aki Shimada, Tokyo (JP); Taisuke Aosaki, Tokyo (JP)

(73) Assignee: Kao Corporation, Tokyo (JP)

( * ) Notice: Subject to any disclaimer, the term of this patent is extended or adjusted under 35 U.S.C. 154(b) by 660 days.

This patent is subject to a terminal disclaimer.

(21) Appl. No.: 17/997,134

(22) PCT Filed: Apr. 28, 2021

(86) PCT No.: PCT/US2021/029577

§ 371 (c)(1),
(2) Date: Oct. 26, 2022

(87) PCT Pub. No.: WO2021/222365

PCT Pub. Date: Nov. 4, 2021

(65) Prior Publication Data

US 2023/0190609 A1 Jun. 22, 2023

Related U.S. Application Data

(60) Provisional application No. 63/017,037, filed on Apr. 29, 2020.

(51) Int. Cl.
*A61K 8/46* (2006.01)
*A61K 8/60* (2006.01)
*A61Q 19/04* (2006.01)

(52) U.S. Cl.
CPC ................ *A61K 8/466* (2013.01); *A61K 8/60* (2013.01); *A61Q 19/04* (2013.01)

(58) Field of Classification Search
CPC . A61K 8/466; A61K 8/60; A61K 8/35; A61Q 19/04
See application file for complete search history.

(56) References Cited

U.S. PATENT DOCUMENTS

| | | | |
|---|---|---|---|
| 4,466,805 A | 8/1984 | Welters et al. | |
| 5,705,145 A | 1/1998 | Miklean et al. | |
| 6,214,322 B1 | 4/2001 | Castro et al. | |
| 7,780,954 B2 | 8/2010 | Polonka et al. | |
| 7,935,331 B2 | 5/2011 | Lin | |
| 2002/0031482 A1 | 3/2002 | Schreier et al. | |
| 2004/0228810 A1 | 11/2004 | Hamson et al. | |
| 2004/0241113 A1 | 12/2004 | Stephens et al. | |
| 2009/0041691 A1 | 2/2009 | Candau et al. | |
| 2011/0229536 A1 | 9/2011 | Kvitnitsky et al. | |
| 2015/0252302 A1 | 9/2015 | Rieth et al. | |
| 2017/0096418 A1 | 4/2017 | Patron et al. | |
| 2017/0216164 A1 * | 8/2017 | Traynor | A61K 8/895 |

FOREIGN PATENT DOCUMENTS

| | | |
|---|---|---|
| EP | 1 764 079 A1 | 3/2007 |
| JP | 2017-186287 A | 10/2017 |
| WO | WO 98/38977 A1 | 9/1998 |

OTHER PUBLICATIONS

International Search Report mailed on Jul. 20, 2021 in PCT/US2021/029577 filed on Apr. 28, 2021 (2 pages).
Written Opinion mailed on Jul. 20, 2021 in PCT/US2021/029577 filed on Apr. 28, 2021 (5 pages).
Extended European Search Report issued Apr. 17, 2024 in European Patent Application No. 21795763.8, 9 pages.
"Anti-Ageing Progressive Glow Moisturiser SPF 20" Database GNPD [Online] Mintel, Jul. 9, 2007, XP093144612, 3 pages.
"Tanning Gel SPF 4" Database GNPD [Online] Mintel, Dec. 20, 2013, XP093144609, 3 pages.
Bath & Body Works, UK, Glow & Steady Moisturising Gradual Tanner, ID#3502765, Mintel GNPD [online], Oct. 2015, [Feb. 7, 2025], Internet <URLhttps://portal.mintel.com>.
Bath & Body Works, USA, Glow & Steady Daily Moisturizer & Gradual Self Tanner SPF 15 for Body, ID#712191, Mintel GNPD [online], May 2007, [Feb. 7, 2025], Internet <URLhttps://portal.mintel.com>.

* cited by examiner

*Primary Examiner* — Jessica Worsham
(74) *Attorney, Agent, or Firm* — Oblon, McClelland, Maier & Neustadt, L.L.P.

(57) ABSTRACT

A topical skincare composition that includes (A) a reducing sugar, (B) an aromatic sulfonate having a topological polar surface area (tPSA) of less than 100 $Å^2$, and (C) a carrier. A method for adjusting color appearance (e.g., hue angle, lightness, saturation) of skin, which involves applying the topical skincare composition onto the skin is also specified. The topical skincare composition can provide a deep, rich, long lasting sunless tan with aesthetically pleasing red/bronze tone when applied onto the skin.

13 Claims, 9 Drawing Sheets

DHA

DHA/NSA

DHA/
Na p-Toluenesulfonate

DHA/
Na Cumenesulfonate

DHA/
Na Polystyrene sulfonate

SELF-TANNING COMPOSITIONS CONTAINING AN AROMATIC SULFONATE AND METHODS THEREOF

BACKGROUND OF THE INVENTION

Field of the Invention

The present invention relates to topical skincare compositions, specifically topical skincare compositions that include (A) a reducing sugar, (B) an aromatic sulfonate, and (C) a carrier, as well as methods of self-tanning using the topical skincare compositions.

Discussion of the Background

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Consumers around the world enjoy spending time in the sun for a variety of reasons including outdoor recreation, sports, and sun tanning (skin darkening). Unfortunately, exposure to UV radiation has known potential to promote skin cancer. Furthermore, partial exposure to UV radiation can lead to uneven skin tone across the body. Health and aesthetic incentives therefore exist for alternative means to achieve natural-looking, even skin tone while avoiding the dangers of sun exposure.

Despite of the known risks, sunbathing remains the most common method to darken skin in the US and the EU. Sunless tanners and glow moisturizers are also common methods, however many consumers are not satisfied with these products, as the colors are often perceived as unnatural, insufficiently dark, or rapidly fading. For example, many conventional self-tanning products using dihydroxyacetone (DHA) as the tanning agent produce an undesirable orange hue. In addition to skin darkening, effective hue modifications are needed to create a prominent tan with bronze/red tones.

Several skin tanning formulations have been reported that utilize azole compounds, pigments (e.g., carmine), cross-linked cationic copolymers, and vanillin polymers for enhanced skin coloration (U.S. Pat. Nos. 5,705,145, 6,214,322, 7,780,954, and 7,935,331, each incorporated herein by reference in its entirety). However, there is still a need for improved formulations capable of effectively darkening the skin color and shifting the hue of the skin.

SUMMARY OF THE INVENTION

In view of the forgoing, there is a demand for a long-lasting topical skincare composition that produces deeper colors and more prominent bronze/red tones.

Accordingly, it is one object of the present invention to provide novel topical skincare compositions that meet these criteria.

It is another object of the present disclosure to provide novel methods of adjusting color appearance (e.g., lightness, hue angle, saturation) of the skin of a subject by topically applying the topical skincare composition onto the skin of the subject.

These and other objects, which will become apparent during the following detailed description, have been achieved by the inventors' discovery that the combination of a reducing sugar, an aromatic sulfonate, and a carrier unexpectedly yields topical skincare compositions that promote long-lasting, rich and intense (i.e., dark) tan color characterized by desirable bronze/red tones.

Thus, the present invention provides:

(1) A topical skincare composition, comprising:

(A) about 0.1 to 30 wt. % of a reducing sugar relative to a total weight of the topical skincare composition;

(B) an alkali metal aromatic sulfonate salt; and (C) a carrier, wherein the alkali metal aromatic sulfonate salt (B) has a topological polar surface area (tPSA) of less than 100 $Å^2$, and wherein a weight ratio of the alkali metal aromatic sulfonate salt (B) to the reducing sugar (A) ((B):(A)) is 1:20 to 20:1.

(2) The topical skincare composition of (1), wherein the alkali metal aromatic sulfonate salt (B) is an optionally substituted phenyl sulfonate, an optionally substituted naphthyl sulfonate, or both.

(3) The topical skincare composition of (1) or (2), wherein the alkali metal aromatic sulfonate salt (B) has no more than 2 hydrogen-bond donor sites.

(4) The topical skincare composition of any one of (1) to (3), wherein the alkali metal aromatic sulfonate salt (B) is sodium 2-naphthalenesulfonate.

(5) The topical skincare composition of any one of (1) to (3), wherein the alkali metal aromatic sulfonate salt (B) is sodium p-toluenesulfonate.

(6) The topical skincare composition of any one of (1) to (3), wherein the alkali metal aromatic sulfonate salt (B) is sodium cumenesulfonate.

(7) The topical skincare composition of any one of (1) to (6), wherein the reducing sugar (A) is dihydroxyacetone, erythrulose, or both.

(8) The topical skincare composition of any one of (1) to (7), wherein the carrier (C) comprises an aromatic alcohol.

(9) The topical skincare composition of any one of (1) to (8), wherein the carrier (C) comprises benzyl alcohol.

(10) The topical skincare composition of any one of (1) to (9), further comprising (D) an organic solvent.

(11) The topical skincare composition of (10), wherein the organic solvent (D) comprises a polyol.

(12) The topical skincare composition of (11), wherein the polyol is at least one selected from the group consisting of 1,3-propanediol, 1,2-propanediol, ethylene glycol, glycerin, and 1,3-butanediol.

(13) The topical skincare composition of any one of (10) to (12), wherein a weight ratio of the carrier (C) to the organic solvent (D) ((C):(D)) is 1:20 to 1:2.

(14) The topical skincare composition of any one of (1) to (13), wherein a weight ratio of the alkali metal aromatic sulfonate salt (B) to the carrier (C) ((B):(C)) is 1:4 to 4:1.

(15) The topical skincare composition of any one of (1) to (14), which is substantially free of a cationic copolymer.

(16) The topical skincare composition of any one of (1) to (15), which is in the form of a lotion, a cream, a gel, a spray, or a foam.

(17) A method of adjusting a color of the skin of a subject, the method comprising: topically applying the topical skincare composition of any one of (1) to (16) onto the skin of the subject, wherein the topical application reduces or increases a hue angle h° of the color by at least 0.5° compared to that prior to the topical application.

(18) A method of adjusting a color of the skin of a subject, the method comprising: topically applying the topical skincare composition of any one of (1) to (16) onto the skin of the subject, wherein the topical application reduces a lightness L* of the color by at least 10% and reduces or increases a hue angle h° of the color by at least 0.5°, each compared to those prior to the topical application.

(19) The method of (18), wherein the topical skincare composition is topically applied to the subject 1 to 3 times daily for 1 to 7 consecutive days.

(20) A method of adjusting a color saturation of the skin of a subject, the method comprising:

topically applying the topical skincare composition of any one of (1) to (16) onto the skin of the subject, wherein the topical application increases a saturation C* of the color by at least 10% compared to that prior to the topical application.

(21) The method of (20), wherein the topical skincare composition is topically applied to the subject 1 to 3 times daily for 1 to 7 consecutive days.

(22) A collection of topical skincare products for retail sale, the collection comprising:

(a) a first topical skincare composition that comprises:

(A) about 0.1 to 30 wt. % of a reducing sugar relative to a total weight of the topical skincare composition;

(B) an alkali metal aromatic sulfonate salt; and (C) a carrier, wherein the alkali metal aromatic sulfonate salt (B) has a topological polar surface area (tPSA) of less than 100 Å$^2$, and wherein a weight ratio of the alkali metal aromatic sulfonate salt (B) to the reducing sugar (A) ((B):(A)) is 1:20 to 20:1, and (b) a second topical skincare composition that comprises:

(A) about 0.1 to 30 wt. % of a reducing sugar relative to a total weight of the topical skincare composition;

(B) an alkali metal aromatic sulfonate salt; and (C) a carrier, wherein the alkali metal aromatic sulfonate salt (B) has a topological polar surface area (PSA) of less than 100 Å$^2$, and wherein a weight ratio of the alkali metal aromatic sulfonate salt (B) to the reducing sugar (A) ((B):(A)) is 1:20 to 20:1, and wherein a content of the reducing sugar (A) present in the first topical skincare composition (a) is less than that of the reducing sugar (A) present in the second skincare composition (b), and wherein the contents are each relative to total weights of the first and second topical skincare compositions.

(23) The collection of (22), wherein the first topical skincare composition (a) and the second topical skincare composition (b) are separately packaged.

(24) A topical skincare composition, comprising:

(A) about 0.1 to 30 wt. % of a reducing sugar relative to a total weight of the topical skincare composition;

(B) an alkali metal aromatic sulfonate salt; and (C) a carrier, wherein the alkali metal aromatic sulfonate salt (B) has a topological polar surface area (tPSA) of less than 100 Å$^2$, wherein the reducing sugar (A) is dihydroxyacetone, erythrulose, or both, wherein the alkali metal aromatic sulfonate salt (B) is an optionally substituted phenyl sulfonate, an optionally substituted naphthyl sulfonate, or both, wherein the carrier (C) comprises an aromatic alcohol, and wherein a weight ratio of the alkali metal aromatic sulfonate salt (B) to the reducing sugar (A) ((B):(A)) is 1:20 to 20:1.

(25) The topical skincare composition of (24), further comprising (D) an organic solvent.

(26) The topical skincare composition of (24), wherein a weight ratio of the alkali metal aromatic sulfonate salt (B) to the carrier (C) ((B):(C)) is 1:4 to 4:1.

(27) The topical skincare composition of (24), which is substantially free of a cationic copolymer.

(28) A topical skincare composition, comprising:

(A) about 0.1 to 10 wt. % of a reducing sugar relative to a total weight of the topical skincare composition;

(B) about 0.1 to 10 wt. % of an alkali metal aromatic sulfonate salt relative to a total weight of the topical skincare composition; and (C) about 0.1 to 5 wt. % of a carrier relative to a total weight of the topical skincare composition, wherein the alkali metal aromatic sulfonate salt (B) has a topological polar surface area (tPSA) of less than 100 Å$^2$, wherein the reducing sugar (A) is dihydroxyacetone, erythrulose, or both, wherein the alkali metal aromatic sulfonate salt (B) is an optionally substituted phenyl sulfonate, an optionally substituted naphthyl sulfonate, or both, wherein the carrier (C) comprises an aromatic alcohol, wherein a weight ratio of the alkali metal aromatic sulfonate salt (B) to the reducing sugar (A) ((B):(A)) is 1:5 to 5:1.

(29) The topical skincare composition of (28), further comprising (D) an organic solvent.

(30) The topical skincare composition of (28), wherein a weight ratio of the alkali metal aromatic sulfonate salt (B) to the carrier (C) ((B):(C)) is 1:4 to 4:1.

(31) The topical skincare composition of (28), which is substantially free of a cationic copolymer.

The foregoing paragraphs have been provided by way of general introduction, and are not intended to limit the scope of the following claims. The described embodiments, together with further advantages, will be best understood by reference to the following detailed description.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE INVENTION

Figure 1A:
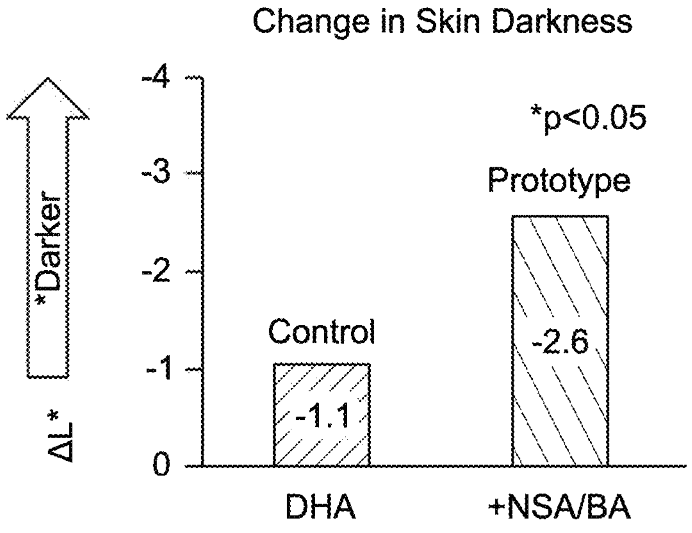
FIG. 1A is a bar graph showing changes in skin darkness (ΔL*) after 4 applications (1 application daily for 4 days) of a control gel ("Control") having 2 wt. % of dihydroxyacetone (DHA) alone, and a prototype gel ("Prototype") containing 2 wt. % of DHA, 2.5 wt. % of sodium 2-naphthalenesulfonate (NSA), and 2.5 wt. % of benzyl alcohol (BA), respectively.
Figure 1B:
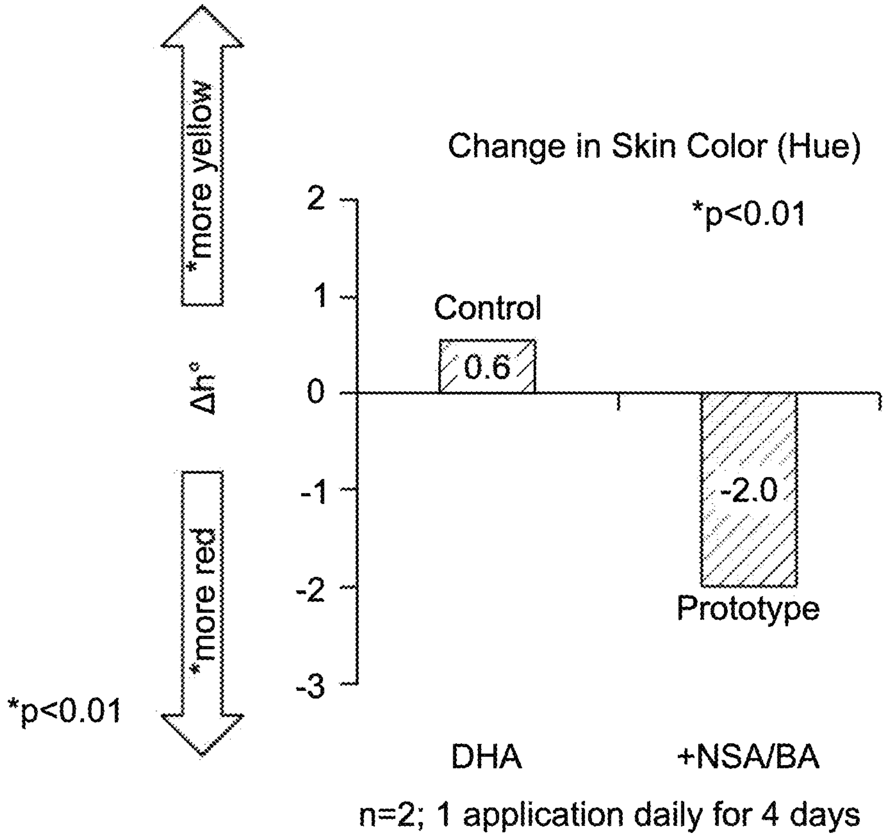
FIG. 1B is a bar graph showing changes in skin hue angle (Δh°) after 4 applications (1 application daily for 4 days) of a control gel ("Control") having 2 wt. % of DHA, and a prototype gel ("Prototype") containing 2 wt. % of DHA, 2.5 wt. % of NSA, and 2.5 wt. % of BA, respectively.
Figure 1C:
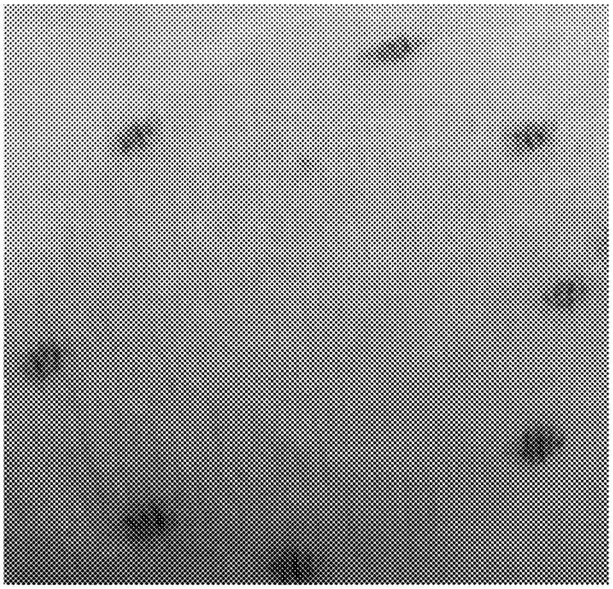
FIG. 1C is a picture showing human skin after 4 applications (1 application daily for 4 days) of a control gel having 2 wt. % of dihydroxyacetone (DHA) alone.
Figure 1D:
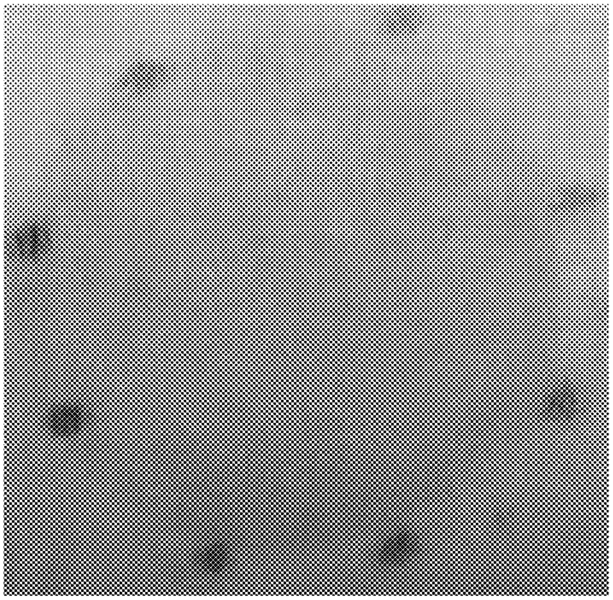
FIG. 1D is a picture showing human skin after 4 applications (1 application daily for 4 days) of a prototype gel containing 2 wt. % of DHA, 2.5 wt. % of sodium 2-naphthalenesulfonate (NSA), and 2.5 wt. % of benzyl alcohol (BA).

In the following description, it is understood that other embodiments may be utilized and structural and operational changes may be made without departure from the scope of the present embodiments disclosed herein.

Definitions

As used herein, the words "a" and "an" and the like carry the meaning of "one or more".

Within the description of this disclosure, where a numerical limit or range is stated, the endpoints are included. Also, all values and subranges within a numerical limit or range are specifically included as if explicitly written out.

When referencing topical skincare compositions, the phrase "substantially free", unless otherwise specified, describes an amount of a particular component present in the topical skincare composition being less than about 1 wt. %, preferably less than about 0.5 wt. %, more preferably less than about 0.1 wt. %, even more preferably less than about 0.05 wt. %, yet even more preferably 0 wt. %, relative to a total weight of the topical skincare composition.

As used herein, the word "about" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), or +/−10% of the stated value (or range of values).

As used herein, the terms "optional" or "optionally" means that the subsequently described event(s) can or cannot occur or the subsequently described component(s) may or may not be present (e.g., 0 wt. %).

As used herein, the term "substituted" refers to at least one hydrogen atom that is replaced with a non-hydrogen group, provided that normal valencies are maintained and that the substitution results in a stable compound.

The term "alkyl", as used herein, unless otherwise specified, refers to a straight, branched, or cyclic, aliphatic fragment having at least 1, preferably at least 2, preferably at least 3, preferably at least 4 carbon atoms and up to 22, preferably up to 20, preferably up to 18, preferably up to 12, preferably up to 8 carbon atoms. Examples of alkyl groups include, but are not limited to, methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl, lauryl, myristyl, cetyl, stearyl, and the like, including guerbet-type alkyl groups (e.g., 2-methylpentyl, 2-ethylhexyl, 2-proylheptyl, 2-butyloctyl, 2-pentylnonyl, 2-hexyldecyl, 2-heptylundecyl, 2-octyldodecyl, 2-nonyltridecyl, 2-decyltetradecyl, and 2-undecylpentadecyl). Cycloalkyl is a type of cyclized alkyl group. Exemplary cycloalkyl groups include, but are not limited to, cyclopropyl, cyclobutyl, cyclopentyl, cyclohexyl, norbornyl, and adamantyl.

As used herein, the term "aryl" refers to an aromatic group containing only carbon in the aromatic ring(s), such as phenyls, biphenyls, naphthyls, anthracenyls, and the like. Exemplary aryls include, but are not limited to, phenyl, 4-methylphenyl (p-tolyl), 2-methylphenyl, 3-methylphenyl, 4-isopropylphenyl, 2-isopropylphenyl, 3-isopropylphenyl, 4-dodecylphenyl, 4-vinylphenyl, 1-naphthyl, and 2-naphthyl.

The term "heteroaryl" is used herein to refer to an aryl group where at least one carbon atom is replaced with a heteroatom (e.g. nitrogen, oxygen, sulfur) and can be indolyl, furanyl, imidazolyl, triazolyl, triazinyl, oxazolyl, isoxazolyl, thiazolyl, isothiazolyl, pyrazolyl, pyrrolyl, pyrazinyl, tetrazolyl, pyridyl (or its N-oxide), thienyl, pyrimidinyl (or its N-oxide), 1H-indolyl, isoquinolyl (or its N-oxide), or quinolyl (or its N-oxide), for example.

The term "alkoxy", as used herein, refers to a straight or branched alkyl group attached to an oxygen atom. Exemplary alkoxy groups include, but are not limited to, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy, and decyloxy.

The term "alkoxycarbonyl" as used in this disclosure refers to an alkoxy group bound to a carbonyl group (i.e., >C═O)).

The term "halogen", as used herein, means fluoro, chloro, bromo and iodo.

As used herein, the term "skin" refers to the skin that exists in humans and other mammals. It is to be recognized that skin exists on many different body parts, and application of the topical skincare compositions herein is not limited to skin found on a specific body part. For example, the topical skincare compositions may be applied to any area of the skin intended for self-tanning, including the face, limbs, feet, neck, torso, and the like. Further, the topical skincare composition may be applied as a moisturizer to the whole body in a daily skin care routine.

Various topical skincare composition ingredients are listed throughout the present disclosure and are organized according to their primary or most desired function, benefit, or use. However, categorization of an ingredient under a particular function, benefit, or use is not meant to limit that ingredient to only that function, benefit, or use. For example, listing of benzyl alcohol as a carrier does not limit the usefulness of benzyl alcohol to only that of a carrier, since benzyl alcohol can also impart other beneficial attributes, such as acting as a preservative and/or a fragrance.

Topical Skincare Composition

The present disclosure is directed to self-tanning topical skincare compositions that modify hue angle, reduce lightness, and increase color saturation of skin appearance. The topical skincare compositions are easy to apply and may be used to darken the color of the skin, shift the tone of the skin, and provide an even and long lasting (fade resistant) tanning coverage.

The topical skincare compositions therefore contain components which enable tanning of the skin and components which facilitate delivery of tanning agents and allow the topical skincare compositions to be easily applied to decrease the lightness and shift the hue of the skin. Such compositions generally include the following components: a tanning agent, which is preferably (A) a reducing sugar, (B) an aromatic sulfonate, (C) a carrier, and optionally (D) an organic solvent, (E) water, (F) a thickening agent, (G) a preservative, and (H) an acidulent. In preferred embodiments, all components are compatible with the reducing sugar (i.e., do not react or cause the reducing sugar to react) and are homogeneously dispersed or dissolved uniformly throughout the topical skincare composition. It has been surprisingly found that the addition of components such as the aromatic sulfonate (B) and the carrier (C) to the reducing sugar (A) enhances the self-tanning effect of the composition, for example, by inducing a change in hue angle (h°) of the skin in addition to decreasing lightness (L*) of the skin.

The topical skincare composition may be in a form of a liquid, a solution, an emulsion, a lotion, a cream, a gel, a paste, a spray, a foam, or any other form that is suitable for topical application to the skin. Preferably, the topical skincare composition is in the form of a lotion, a cream, a gel, a spray, or a foam. More preferably, the topical skincare composition is in the form of a cream or a gel that can be evenly applied.

Tanning Agent

To act as an effective self-tanner, the topical skincare composition herein includes a "tanning agent", which is any colored molecule that is capable of staining the skin when it is brought into contact with the skin, or any non-colored molecule that is capable of reacting with and coloring the skin, in particular, a molecule capable of darkening the skin so that it resembles the darkening effect achieved by exposure of one's skin to solar radiation (i.e., a natural tan).

In preferred embodiments, the tanning agent is (A) a reducing sugar. Certain reducing sugars such as monosaccharides (e.g. dihydroxyacetone) react with amino acids naturally occurring on the skin surface and, by virtue of a Maillard reaction, form pigmented melanoidins that cause the skin to change color (Bobin et al. J. Soc. Cosmet. Chem., 35 pages 265-272, 1984; Maillard L. C., C. R. Acad. Sci. 154, 66-68,1912—each incorporated herein by reference in its entirety).

Different amino acids react with different reducing sugars differently to produce a variety of tones of coloration from yellow to brown. Any reducing sugar capable of reacting with amino acids found in skin (e.g., naturally occurring amino acids) to produce a darkened skin, can be employed as the tanning agent herein. The reducing sugar (A) may be a monosaccharide which is an aldose having 2 to 6 carbon atoms, preferably 3 to 5 carbon atoms, more preferably 3 to 4 carbon atoms, even more preferably 3 carbon atoms, a ketose having 3 to 6 carbon atoms, preferably 4 to 5 carbon atoms, more preferably 3 to 4 carbon atoms, including mixtures such aldoses and/or ketoses. Exemplary reducing sugars include, but are not limited to, dihydroxyacetone (DHA), erythrulose, glycolaldehyde, glyceraldehyde, meso-tartaric aldehyde, glucose, gulose, xylose, fructose, ribose, arabinose, allose, talose, altrose, idose, mannose, galactose, and erythrose. In preferred embodiments, the reducing sugar (A) is dihydroxyacetone, erythrulose, or both. Most preferably, the reducing sugar (A) is dihydroxyacetone. Dihydroxyacetone is available, for example, from EMD Millipore.

The amount of tanning agent present in the topical skincare composition may vary depending on the skin coloration (e.g., lightness, hue angle, color saturation) desired and the quantity and nature of the other components. In some embodiments, the tanning agent is present in amounts of at least about 0.05 wt. %, preferably at least about 0.1 wt. %, preferably at least about 0.5 wt. %, preferably at least about 1 wt. %, more preferably at least about 1.5 wt. %, even more preferably at least about 1.75 wt. %, yet even more preferably at least about 2 wt. %, and up to about 10 wt. %, preferably up to about 8 wt. %, preferably up to about 6 wt. %, preferably up to about 4 wt. %, preferably up to about 3.5 wt. %, more preferably up to about 3 wt. %, even more preferably up to about 2.5 wt. %, yet even more preferably up to about 2.25 wt. %, based on a total weight of the topical skincare composition.

In preferred embodiments, the topical skincare compositions are substantially free of tanning agents besides reducing sugars, which includes being substantially free of, preferably completely free of (i.e., 0 wt. %) synthetic dyes and natural pigments which provide color. Alternatively, the topical skincare compositions may include other tanning agent such as synthetic dyes and/or natural pigments in amounts listed previously.

Examples of synthetic dyes which may be incorporated as a tanning agent include, but are not limited to acid dyes (e.g., Yellow No. 203 (D&C Yellow No. 10, color index (CI) given as CI 47005), Orange No. 205 (D&C Orange No. 4, CI 15510), Red No. 3 (Erythrosin B, CI 45430), Red No. 94 (Bengal rose, CI 45440), and Red No. 227 (D&C Red No. 33, CI 17200)); quinone-based dyes (e.g., anthraquinone, 1-N-methylmorpholiniumpropylamino-4-hydroxyanthraquinone, 1-aminopropylamino-4-methylaminoanthraquinone, 1-aminopropylaminoanthraquinone, 5-β-hydroxyethyl-1,4-diaminoanthraquinone, 2-aminoethylaminoanthraquinone, 1,4-bis (β,γ-dihydroxypropylamino) anthraquinone, lawsone, juglone, alizarin, purpurin, carminic acid, carmine, kermesic acid, spinulosin, Disperse Red 15, Solvent Violet 13, Disperse Violet 1, Disperse Violet 4, Disperse Blue 1, Disperse Violet 8, Disperse Blue 3, Disperse Red 11, Disperse Blue 7, Basic Blue 22, Disperse Violet 15, Basic Blue 99); azo-based dyes (e.g., 1,3-dimethyl-2-[[4-(dimethylamino)phenyl]azo]-1H-imidazolium chloride, 1,3-dimethyl-2-[(4-aminophenyl] azo]-1H-imidazolium chloride, 1-methyl-4-[(methylphenylhydrazono)methyl]pyridinium methyl sulfate, Disperse Red 17, Basic Red 22, Basic Red 76, Basic Yellow 57, Basic Brown 16, Basic Brown 17, Disperse Black 9); and indoamine-based dyes (e.g., 2-β-hydroxyethylamino-5-[bis (β-4'-hydroxyethyl) amino]anilino-1,4-benzoquinone, 2-β-hydroxyethylamino-5-(2'-methoxy-4'-amino) anilino-1,4-benzoquinone, 3-N-(2'-chloro-4'-hydroxy)phenylacetamino-6-methoxy-1,4-benzoquinoneimine, 3-N-(3'-chloro-4'-methylamino)phenylureido-6-methyl-1,4-benzoquinoneimine, 3-[4'-N-(ethylcarbamylmethyl)amino] phenylureido-6-methyl-1,4-benzoquinoneimine).

The topical skincare composition may include a natural pigment as a tanning agent. Non-limiting examples of natural dyes include caramels, beta-carotenes, beet root extracts, blue green algae, cocoa powder, walnut extracts, melanin, and curcumin.

(B) Aromatic Sulfonate

The topical skincare composition of the present disclosure may include an aromatic sulfonate (B). Preferably, the aromatic sulfonate (B) has formula (I)

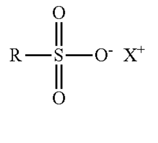

(I)

or a solvate thereof, a tautomer thereof, a stereoisomer thereof, or a mixture thereof, wherein (i) R is an optionally substituted aryl or an optionally substituted heteroaryl, and (ii) X is a cation selected from the group consisting of hydrogen ion, ammonium ion, and an alkali metal ion.

The term "cation" means a positively charged ion including, but not limited to, hydrogen ion, ammonium ion (i.e., $NH_4^+$), quaternary ammonium ion (e.g., tetraethyl ammonium, tetrabutyl ammonium), lithium ion, sodium ion, potassium ion, and silver ion. Preferably, the aromatic sulfonate (B) is an alkali metal aromatic sulfonate salt. In preferred embodiments, X is an alkali metal ion such as lithium ion, sodium ion, and potassium ion. Most preferably, X is sodium ion.

The aromatic sulfonate (B) may be an optionally substituted phenyl sulfonate, an optionally substituted naphthyl sulfonate, or both. In preferred embodiments, R is an optionally substituted aryl. In some embodiments, R is an optionally substituted phenyl. In some embodiments, R is an optionally substituted naphthyl. R may be an aryl or heteroaryl substituted with at least one substituent such as an optionally substituted alkyl, an alkoxy, an alkoxycarbonyl, carboxy, an amino, hydroxy, thiol, halogen, cyano, and nitro. Alternatively, R may be an aryl or heteroaryl which is unsubstituted.

In some embodiments, R is an aryl or heteroaryl substituted with at least one linear, branched, or cyclic alkyl group having at least 1, preferably at least 2, preferably at least 3, preferably at least 4, preferably at least 5 carbon atoms and up to 14, preferably up to 12, preferably up to 10, preferably up to 8, preferably up to 6 carbon atoms. In preferred embodiments, R is an aryl or heteroaryl substituted with at least one linear alkyl, such as methyl, ethyl, n-propyl, n-butyl, n-pentyl, n-hexyl, n-heptyl, n-octyl, n-decyl, and n-dodecyl. In preferred embodiments, R is substituted with at least one branched alkyl, such as isopropyl, sec-butyl, isobutyl, isobutyl, tert-butyl, isopentyl, neopentyl, and isohexyl. Most preferably, R is substituted with methyl or isopropyl.

Disadvantages associated with using common reducing sugars (e.g., dihydroxyacetone, erythrulose) by themselves as tanning agents include insufficient coloration, unwanted orange undertone, rapidly fading coloration, and uneven coverage. It has been unexpectedly discovered that a combination of a reducing sugar (A) (e.g., dihydroxyacetone), an aromatic sulfonate (B), and a carrier (C), as discussed below, provides an intense, long-lasting artificial tan with aesthetically pleasing red/bronze tone. Without being bound by theory, it is believed that the aromatic sulfonate (B) herein promotes advanced Maillard reaction by aiding polymerization of melanoidins with a higher degree of polymerization and/or conjugation, thereby producing an intensely-colored and fade resistant tan with hue adjustment.

Exemplary aromatic sulfonates include, but are not limited to, phenyl sulfonates such as sodium benzenesulfonate, sodium p-toluenesulfonate, sodium cumenesulfonate (i.e., sodium 4-isopropylbenzenesulfonate), sodium 2,3-dimethylbenzenesulfonate, sodium 2,5-dimethylbenzenesulfonate, 2,4,6-trimethylbenzenesulfonate, sodium 4-ethylbenzenesulfonate, sodium 4-propylbenzenesulfonate, sodium 4-tert-butylbenzenesulfonate, sodium 4-chlorobenzenesulfonate, sodium 4-bromobenzenesulfonate, sodium 4-hydroxybenzenesulfonate, sodium dodecylbenzenesulfonate, sodium 3-sulfobenzoate, potassium 4-sulfobenzoate, 4-amino-3,5-dibromobenzenesulfonic acid sodium salt, 4-octylbenzenesulfonic acid sodium salt, and 4-dodecylbenzenesulfonic acid sodium salt; naphthyl sulfonates such as sodium 1-naphthalenesulfonate, sodium 2-naphthalenesulfonate, sodium 2-methyl-1-naphthalenesulfonate, sodium 4-methyl-1-naphthalenesulfonate, sodium 2-butyl-1-naphthalenesulfonate, sodium 4-hydroxy-1-naphthalenesulfonate, sodium 4-amino-1-naphthalenesulfonate, sodium 6-hydroxy-2-naphthalenesulfonate, and sodium 5-amino-1-naphthalenesulfonate, and mixtures thereof.

In some embodiments, polymers or oligomers containing the aromatic sulfonate of formula (I) as a repeating unit, for example poly(sodium 4-styrenesulfonate), poly(4-styrenesulfonic acid) ammonium salt, poly(4-styrenesulfonic acid), poly(sodium 2-styrenesulfonate), and sodium polyanethole-sulfonate, may be used in lieu of, or in addition to the aforementioned aromatic sulfonates.

In preferred embodiments, the aromatic sulfonate (B) is at least one selected from the group consisting of sodium 2-naphthalenesulfonate, sodium p-toluenesulfonate, sodium cumenesulfonate, 4-dodecylbenzenesulfonic acid sodium salt, and poly(sodium 4-styrenesulfonate, more preferably at least one selected from the group consisting of sodium 2-naphthalenesulfonate (available from Sugai Chemical), sodium p-toluenesulfonate, and sodium cumenesulfonate.

As used herein, topological polar surface area (tPSA) of a molecule is defined as the sum of surface contributions of polar atoms (e.g., oxygen and nitrogen atoms, as well as bonded hydrogen atoms) in the molecule. Methods of calculating tPSA are known by those of ordinary skill in the art (see, e.g., Ertl, P., et al., "Fast calculation of molecular polar surface area as a sum of fragment based contributions and its application to the prediction of drug transport properties", J. Med. Chem. 2000, 43, 3714-3717, hereby incorporated by reference in its entirety). For example, tPSA can be determined using a desktop computer and commercially available chemical graphic software, such as ChemAxon-Marvinview and ChemDraw. Alternatively, tPSA can be found on many chemical databases, such as SciFinder.

Aromatic sulfonates (B) useful in the present disclosure have a topological polar surface area (tPSA) of less than 100 $Å^2$, for example, from about 20 $Å^2$, preferably from about 30 $Å^2$, more preferably from about 40 $Å^2$, even more preferably from about 50 $Å^2$, and up to about 95 $Å^2$, preferably up to about 90 $Å^2$, preferably up to about 80 $Å^2$, preferably up to about 70 $Å^2$, more preferably up to about 65 $Å^2$, even more preferably up to about 60 $Å^2$.

As used herein, hydrogen-bond donor sites are functionalities having hydrogen atoms which are readily coordinated with an electronegative atom such as oxygen, nitrogen, and sulfur. Exemplary hydrogen-bond donor sites include hydroxy, carboxylic acid, thiol, sulfonic acid, primary amines, secondary amines, and N—H functionalities in amides. In preferred embodiments, the aromatic sulfonate (B) has up to 2 hydrogen-bond donor sites, preferably up to 1 hydrogen-bond donor site, more preferably 0 hydrogen-bond donor sites.

While not wishing to be bound by theory, aromatic sulfonates (B) with a lower tPSA value and/or a smaller number of hydrogen-bond donors may have better skin permeability and higher dermal absorption, which can be advantageous for self-tanning skincare formulations.

In some embodiments, the aromatic sulfonate (B) is present in amounts of at least about 0.05 wt. %, preferably at least about 0.1 wt. %, preferably at least about 0.5 wt. %, preferably at least about 1 wt. %, more preferably at least about 1.5 wt. %, even more preferably at least about 2 wt. %, yet even more preferably at least about 2.5 wt. %, and up to about 10 wt. %, preferably up to about 8 wt. %, preferably up to about 6 wt. %, preferably up to about 5 wt. %, preferably up to about 4 wt. %, more preferably up to about 3.5 wt. %, even more preferably up to about 3 wt. %, yet even more preferably up to about 2.75 wt. %, based on a total weight of the topical skincare composition.

(C) Carrier

The topical skincare compositions of the present disclosure may include a carrier (C), which is a material capable of enhancing uniform delivery and penetration of the tanning agent (and other components of the topical skincare composition) into the skin so that a deeper, richer, and longer-lasting tan can be achieved.

Examples of carriers (C) suitable for use herein include, but are not limited to, benzyl alcohol, 2-phenylethyl alcohol, phenoxyethanol, methanol, ethanol, n-propanol, iso-propanol, n-butanol, sec-butanol, iso-butanol, tert-butanol, hexanol, n-octanol, 2-octanol, 2-ethyl hexonal, diethylene glycol monoethyl ether, diethylene glycol monobutyl ether, and mixtures thereof.

In some embodiments, the carrier (C) comprises an aromatic alcohol. Because of the presence of a polar end (hydroxy group) and a non-polar end (phenyl group), aromatic alcohols (e.g., benzyl alcohol, 2-phenylethyl alcohol, phenoxyethanol) may enable a more effective transdermal delivery of the tanning agent (and other components of the topical skincare composition) than other short chain alkyl alcohols, such as ethanol and n-butanol. Furthermore, benzyl alcohol is particularly advantageous because of its moderate water solubility, aromatic odor, antimicrobial properties, and low toxicity. In preferred embodiments, the carrier (C) used herein comprises benzyl alcohol, 2-phenylethyl alcohol, 1-phenylethanol, phenoxyethanol, or mixtures thereof. Most preferably, the carrier (C) comprises, or consists essentially of benzyl alcohol (available from Emerald Kalama Chemical).

In some embodiments, the amount of carrier (C) present in the topical skincare composition is from about 0.1 wt. %, preferably from about 0.5 wt. %, preferably from about 1 wt. %, preferably from about 1.5 wt. %, preferably from about 2 wt. %, and up to about 5 wt. %, preferably up to about 4 wt. %, preferably up to about 3 wt. %, preferably up to about 2.5 wt. %, based on a total weight of the topical skincare composition.

The weight ratios among the reducing sugar (A) (e.g., dihydroxyacetone), the aromatic sulfonate (B) (e.g., sodium 2-naphthalenesulfonate, sodium p-toluenesulfonate), and the carrier (C) (e.g., benzyl alcohol) may be varied depending on tanning color shade (e.g., darkness, hue angle, color saturation). However, typically, a weight ratio of the aromatic sulfonate (B) to the reducing sugar (A) ((B):(A)) is from 1:20, preferably from 1:15, preferably from 1:10, preferably from 1:8, preferably from 1:6, preferably from 1:5, preferably from 1:4, preferably from 1:3, more preferably from 1:2, even more preferably from 2:3, yet even more preferably from 1:1, and up to 20:1, preferably up to 15:1, preferably up to 10:1, preferably up to 8:1, preferably up to 6:1, preferably up to 5:1, preferably up to 4:1, preferably up to 3:1, more preferably up to 2:1, even more preferably up to 3:2, yet even more preferably up to 5:4.

In some embodiments, a weight ratio of the aromatic sulfonate (B) to the carrier (C) ((B):(C)) is from 1:4, preferably from 2:7, preferably from 1:3, preferably from 2:5, more preferably from 1:2, even more preferably from 2:3, yet even more preferably from 1:1, and up to 4:1, preferably up to 7:2, preferably up to 3:1, preferably up to 5:2, more preferably up to 2:1, even more preferably up to 3:2, yet even more preferably up to 5:4.

(D) Organic Solvent

The topical skincare composition may optionally include an organic solvent (D), which is structurally different from the carrier (C). The organic solvent (D) may aid solubilization of components not sufficiently soluble in the aforementioned carrier, adjust the surface property of the topical skincare composition for enhanced workability, viscosity, and/or ease of handling, or to generally provide a medium that is suitable for self-tanning operations. Examples of organic solvents useful for the present disclosure include, but are not limited to, polyols, for example, ethylene glycol, propylene glycol (e.g., 1,3-propanediol, 1,2-propanediol), butylene glycol (e.g., 1,3-butanediol, 1,2-butanediol, 1,4-butanediol, 2,3-butanediol), hexylene glycol, isoprene glycol, diethylene glycol, dipropylene glycol, glycerin, polyol ethers, for example, ethylene glycol monomethyl ether, ethylene glycol monoethyl ether, propylene glycol monomethyl ether, diethylene glycol monomethyl ether, diethylene glycol monoethyl ether), and a $C_1$ to $C_4$ lower alkanol, for example, methanol, ethanol, isopropanol, butanol, as well as mixtures thereof. In some embodiments, the organic solvent (D) comprises a polyol which is at least one selected from the group consisting of 1,3-propanediol, 1,2-propanediol, ethylene glycol, glycerin, and 1,3-butanediol (available from OXEA). In preferred embodiments, the organic solvent (D) is 1,3-propanediol.

Alternatively, a mixture of polyols is used as the organic solvent (D), for example a mixture of a first polyol and a second polyol which is different from the first polyol. In some embodiments, the first polyol is 1,3-propanediol. In some embodiments, the second polyol is glycerin. When a mixture of the first polyol (e.g., 1,3-propanediol) and the second polyol (e.g., glycerin) is used, a weight ratio of the first polyol to the second polyol may be typically from 1:6, preferably from 1:5, preferably from 1:4, preferably from 1:3, more preferably from 1:2, more preferably from 1:1, even more preferably from 3:2, yet even more preferably from 2:1, and up to 10:1, preferably up to 8:1, preferably up to 6:1, more preferably up to 5:1, even more preferably up to 4:1, yet even more preferably up to 3:1.

When present, the organic solvent (D) may be included in the topical skincare compositions in an amount ranging from about 0.2 wt. %, preferably from about 0.5 wt. %, more preferably from about 1 wt. %, preferably from about 2 wt. %, more preferably from about 3 wt. %, even more preferably from about 4 wt. %, yet even more preferably from about 5 wt. %, and up to about 20 wt. %, preferably up to about 15 wt. %, preferably up to about 12 wt. %, more preferably up to about 10 wt. %, even more preferably up to about 8 wt. %, yet even more preferably up to about 6 wt. %, based on a total weight of the topical skincare composition.

A weight ratio of the carrier (C) (e.g., benzyl alcohol) to the organic solvent (D) (e.g., 1,3-propanediol, ethylene glycol, glycerin) may range from 1:200, preferably from 1:150, preferably from 1:100, preferably from 1:50, preferably from 1:25, preferably from 1:20, preferably from 1:10, more preferably from 1:8, even more preferably from 1:6, yet even more preferably from 1:5, and up to 25:1, preferably up to 20:1, preferably up to 15:1, preferably up to 10:1, preferably up to 5:1, preferably up to 3:1, preferably up to 2:1, preferably up to 1:1, more preferably up to 1:2, even more preferably up to 1:3, yet even more preferably up to 1:4.

(E) Water

In some embodiments, the topical skincare composition of the present disclosure is an aqueous composition or an oil-in-water (o/w) emulsion where the continuous phase is aqueous. Therefore, in preferred embodiments, the topical skincare composition further includes water (E) in amounts of at least about 10 wt. %, preferably at least about 20 wt. %, preferably at least about 30 wt. %, preferably at least about 40 wt. %, more preferably at least about 50 wt. %, even more preferably at least about 60 wt. %, yet even more preferably at least about 70 wt. %, and up to about 95 wt. %, preferably up to about 90 wt. %, more preferably up to about 85 wt. %, even more preferably up to about 80 wt. %, based on a total weight of the topical skincare composition.

(F) Thickening Agent

The topical skincare composition may optionally include a thickening agent (F) that may improve stability of the composition as well as yield a consistency that is soothing to the skin upon application.

The thickening agent (F) may comprise a copolymer which contains, as a structural unit, at least one selected from the group consisting of a hydroxyalkyl acrylate, an acrylic acid salt, acrylamide, and an acryloyldialkyl taurate. Examples of thickening copolymers include a copolymer of hydroxyethyl acrylate and sodium acryloyldimethyl taurate, a copolymer of acrylate and sodium acryloyldimethyl taurate, a copolymer of acrylamide and acrylate, and a copolymer of acrylic acid, acrylamide, acrylate, and sodium acryloyldimethyl taurate. Preferably, the thickening agent (F) contains an anionic (co) polymer.

These thickening copolymers are commercially available, for example from SEPPIC, France. Exemplary thickening agents containing a copolymer of hydroxyethyl acrylate and acryloyldimethyl taurate include SEPINOV™ EMT 10 (hydroxyethyl acrylate/sodium acryloyldimethyl taurate copolymer), SIMULGEL™ NS (hydroxyethyl acrylate/sodium acryloyldimethyl taurate copolymer, squalane, polysorbate 60), SIMULGEL™ FL (hydroxyethyl acrylate/sodium acryloyldimethyl taurate copolymer, isohexadecane, polysorbate 60), SEPIPLUS™ S (hydroxyethyl acrylate/sodium acryloyldimethyl taurate copolymer, polyisobutene, PEG-7 trimethylolpropane coconut ether), and SIMULGEL™ INS 100 (hydroxyethyl acrylate/sodium acryloyldimethyl taurate copolymer, Isohexadecane, polysorbate 60). Exemplary thickening agents containing a copolymer of acrylate and acryloyldimethyl taurate include SIMULGEL™ EG (sodium acrylate/sodium acryloyldimethyl taurate copolymer, isohexadecane, polysorbate 80), SIMULGEL™ EPG (sodium acrylate/sodium acryloyldimethyl taurate copolymer, polyisobutene, caprylyl capryl glucoside), and SIMULGEL™ SMS 88 (sodium acrylate/acryloyldimethyl taurate/dimethyacrylamide cross-polymer, isohexadecane, polysorbate 60). An example of thickening agent containing a copolymer of acrylamide and acrylate include SEPIPLUS™ 265 (acrylamide/ammonium acrylate copolymer, polyisobutene, polysorbate 20). An example of thickening agent containing a copolymer of acrylic acid, acrylamide, acrylate, and acryloyldimethyl taurate includes SEPIPLUS™ 400 (polyacrylate-13, polyisobutene, polysorbate 20).

In some embodiments, the thickening agent (F) contains a copolymer of hydroxyethyl acrylate and a sodium acryloyldimethyl taurate. More preferably, the thickening agent is SEPIPLUS™ S (hydroxyethyl acrylate/sodium acryloyldimethyl taurate copolymer, polyisobutene, PEG-7 trimethylolpropane coconut ether).

Other thickening materials that may be used in addition to, or in lieu of the aforementioned thickening agents include carbomers (e.g., Carbomer 980), $C_{10-30}$ alkylacrylate crosspolymers (e.g., Pemulen TR-1, Pemulen TR-2 (acrylates/$C_{16-30}$ alkyacrylates cross-polymer)), SEPIGEL™ 305 (Polyacrylamide, $C_{13-14}$ isoparaffin, laureth-7), SIMULGEL™ A (ammonium polyacrylate, isohexadecane, PEG-40 castor oil), SIMULGEL™ 600 (acrylamide/sodium acryloyldimethyl taurate copolymer, isohexadecane, polysorbate 80), ARISTOFELX® AVC (ammonium acryloyldimthyltaurate/N-vinylpyrrolidone copolymer), ARISTOFELX® AVS (sodium acryloyldimethyltaurate/N-vinylpyrrolidone copolymer), and modified cellulose polymers (e.g., hydroxyethyl cellulose, methyl cellulose).

A cationic copolymer, as used herein, unless otherwise specified, refers to a copolymer that incorporates a cationic monomer which is a methacryloylethyl tri($C_1$-$C_3$ alkyl)

ammonium salt or an acryloylethyl tri($C_1$-$C_3$ alkyl) ammonium salt (e.g., acryloylethyl trimethylammonium chloride) as one of the repeating units. Exemplary monomers that may be utilized in forming the cationic copolymer with the methacryloylethyl tri($C_1$-$C_3$ alkyl) ammonium salt or the acryloylethyl tri($C_1$-$C_3$ alkyl) ammonium salt include acrylamide, methacrylamide, tris (hydroxymethyl)-acrylamidomethane, and those disclosed in U.S. Pat. No. 7,780,954—which is incorporated herein by reference in its entirety.

In preferred embodiments, the topical skincare compositions are substantially free of the cationic copolymer, which includes being substantially free of, preferably completely free of (i.e., 0 wt. %) the aforementioned cationic copolymer, such as acrylamide/acryloylethyl trimethylammonium chloride/tris (hydroxymethyl)-acrylamidomethane copolymer.

(G) Preservative

The topical skincare composition may optionally further include a preservative (G). For example, the preservative may be selected to kill bacteria that might otherwise be sustained or multiplied in the composition, or to prevent degradation or chemical breakdown (e.g., oxidative degradation) of the composition. Preservatives suitable for use in cosmetic formulations are well-known to those of ordinary skill in the art. In this respect, the preservative chosen may be varied depending on the particular components present in the topical skincare composition. Illustrative of suitable preservatives include methylparaben, ethylparaben, propylparaben, EDTA or salts thereof (such as disodium EDTA), phenoxyethanol, DMDM hydantoin, benzyl alcohol, ethyldibromoglutaronitrile-phenoxyethanol/polyquaternium-7 (Euxyl K-400, Calgon), imidazolidinyl urea, diazolidinyl urea, benzalkonium chloride, benzethonium chloride, sodium benzoate, sorbic acid and the like, or combinations thereof.

Preferably, the preservative (G) is methylparaben and/or ethylparaben, most preferably a mixture of these preservatives. When present, the preservative (G) may be included herein in amounts of up to about 5 wt. %, preferably up to about 4 wt. %, preferably up to about 3 wt. %, preferably up to about 2 wt. %, preferably up to about 1 wt. %, preferably up to about 0.5 wt. %, for example from about 0.001 wt. % to about 3 wt. %, or 0.1 wt. % to about 1.5 wt. %, or 0.15 wt. % to about 1 wt. %, or 0.3 wt. % to about 0.45 wt. %, based on a total weight of the topical skincare composition.

(H) Acidulant

The topical skincare compositions disclosed herein may be optionally formulated to include an acidulant (H) for adjusting the pH to be more acidic/less alkaline. Additionally, depending on the chemical structure, the acidulant (H) may act as a chelating agent and/or a buffering agent to neutralize minerals, enhance the activity of any preservatives present, and to stabilize active ingredients (e.g., the tanning agent).

The acidulant employed herein may be an inorganic acid or an organic acid, and specifically includes, but is not limited to, hydrochloric acid, orthophosphoric acid, sulfuric acid, carboxylic acids such as fumaric acid, acetic acid, and α-hydroxy acids such as tartaric acid, citric acid, malic acid, lactic acid, and glycolic acid, as well as mixtures thereof. When the acidulant contains α-hydroxy acid functionality, the acidulant may also aid in exfoliating the skin and softening wrinkles. Preferably citric acid is used.

When present, the acidulant (H) may be included herein in amounts of up to about 5 wt. %, preferably up to about 4 wt. %, preferably up to about 3 wt. %, preferably up to about 2 wt. %, preferably up to about 1 wt. %, for example from about 0.001 wt. % to about 3 wt. %, or 0.02 wt. % to about 2 wt. %, or 0.1 wt. % to about 1 wt. %, or 0.2 wt. % to about 0.5 wt. %, based on a total weight of the topical skincare composition. The pH of the topical skincare composition may be varied, but is preferably less than 6.5, for example, at least 2, preferably at least 2.5, more preferably at least 3, even more preferably at least 3.5, and up to 6, preferably up to 5, more preferably up to 4.

Other Optional Ingredients

Various optional ingredients frequently used in topical formulations such as fragrances, propellants, vehicles, adjuvants, anti-aging components, proteins, rheology control agents, dispersants, thickeners, film-forming agents, sequestering agents, cleansing agents, vitamins, botanicals, and sunscreen agents, as well as other classes of materials whose presence may be cosmetically, medicinally or otherwise desirable, can also optionally be included at their conventional art-established usage levels. For example, the topical skincare compositions of the present disclosure may be optionally formulated to include one or more fragrances known to those of ordinary skill in the cosmetics arts to impart a pleasant scent or to help mask any malodorous components that may be present in the topical skincare compositions.

In preferred embodiments, the topical skincare compositions are substantially free of such optional ingredients, however, when included, non-limiting examples which can be used include film-forming materials such as petrolatum, hydrolyzed wheat protein/wheat oligosaccharides (e.g., Cropeptide W by Croda Inc.), hydrolyzed corn protein, hydrolyzed wheat gluten, hydrolyzed yeast protein, hydrolyzed vegetable protein, hydrolyzed soy protein, hydrolyzed rice protein, and hydrolyzed potato protein; moisturizers such as glycereth-7-triacetate (Dermol GL-7-A, Alzo), glycereth-5-lactate, and glycereth-7-diisononanoate; skin conditioning agents and emollients such as mineral oil, cetearyl alcohol, silicones, for example, dimethicone, cyclomethicone, phenyltrimethicone, alkyl dimethicone, fluorinated silicones, esters of isononanoic acid, for example, ethylhexyl isononanoate, butylene glycol diisononanoate, cetearyl isononanoate, and cetyl isononanoate, and polyethylene glycol derivatives of castor oil, for example, PEG-40 castor oil (Surfactol 365, available from Vertellus), PEG-45 castor oil, PEG-50 castor oil, PEG-60 castor oil, and PEG-100 castor oil; surfactants such as polyoxyalkylene ethers of a fatty alcohol, for example, laureth-3, ceteareth-6, ceteareth-11, ceteareth-15, ceteareth-16, ceteareth-17, ceteareth-18, ceteareth-20, ceteareth-23, ceteareth-25, ceteareth-27, ceteareth-28, ceteareth-30, isoceteth-20, laureth-9/myreth-9, and PPG-3 caprylyl ether, steareths (steareth-2, steareth-4, steareth-6, steareth-7, steareth-10, steareth-11, steareth-13, steareth-15, steareth-20), and polyethylene glycol esters, for example, PEG-14 laurate, PEG-15 laurate, PEG-20 laurate, PEG-32 laurate, PEG-75 laurate, PEG-150 laurate or other surfactants; and sunscreens or UV light absorbing compounds such as octyldimethyl PABA, benzophenone-4, DEA methoxycinnamate, 2-phenyl-benzimidazole-5-sulfonic acid, and triethanolamine salicylate.

In preferred embodiment, the topical skincare composition includes 1 to 3 wt. % of a reducing sugar (A) (e.g., dihydroxyacetone, erythrulose), 1 to 3 wt. % of an aromatic sulfonate (B) (e.g., sodium 2-naphthalenesulfonate, sodium p-toluenesulfonate, or both), 1 to 3 wt. % of a carrier (C) (e.g., benzyl alcohol), 2 to 8 wt. % of an organic solvent (D) (e.g., 1,3-propanediol, 1,2-propanediol, ethylene glycol, glycerin, 1,3-butanediol), and 70 to 82 wt. % water (E), each based on a total weight of the topical skincare composition, with the balance optionally including one or more of a preservative (G) (e.g., a mixture of methylparaben and ethylparaben), an acidulent (H) (e.g., citric acid), and a thickening agent (F) (e.g., SEPIPLUS S (hydroxyethyl acrylate/sodium acryloyldimethyl taurate copolymer, polyisobutene, PEG-7 trimethylolpropane coconut ether).

In preferred embodiments, the topical skincare composition includes 1 to 3 wt. % of a reducing sugar (A) (e.g., dihydroxyacetone), 1 to 3 wt. % of an aromatic sulfonate (B) (e.g., sodium 2-naphthalenesulfonate, sodium p-toluenesulfonate, or both), 1 to 3 wt. % of a carrier (C) (e.g., benzyl alcohol), 2 to 8 wt. % of an organic solvent (D) (e.g., 1,3-propanediol, 1,2-propanediol, ethylene glycol, glycerin, 1,3-butanediol), 70 to 82 wt. % water (E), 0.001 to 1 wt. % of a preservative (G) (e.g., a mixture of methylparaben and ethylparaben), 0.001 to 0.2 wt. % of an acidulent (H) (e.g., citric acid), and 1 to 3 wt. % of a thickening agent (F) (e.g., SEPIPLUS™ S (hydroxyethyl acrylate/sodium acryloyldimethyl taurate copolymer, polyisobutene, PEG-7 trimethylolpropane coconut ether), each based on a total weight of the topical skincare composition.

The topical skincare compositions herein can be prepared via any method known to those of ordinary skill in the art. By way of example, the topical skincare composition that contains water may be prepared by (i) mixing together all water soluble ingredients except for the tanning agent (e.g., the reducing sugar) in an appropriately sized vessel with water with optional heating (e.g., 40 to 90° C., preferably 50 to 85° C., more preferably 75 to 81° C.) and agitation until homogenous, (ii) in a separate vessel, mixing all oil phase ingredients, if any, with optional heating (e.g., 40 to 90° C., preferably 50 to 85° C., more preferably 75 to 81° C.) and stirring until homogeneous, (iii) mixing together the homogenous mixture from (i) with the homogenous mixture from (ii), if any, with optional heating (e.g., 40 to 90° C., preferably 50 to 85° C., more preferably 75 to 81° C.) and agitation until a homogenous aqueous composition or uniform oil in water emulsion is formed, (iv) cooling down the homogenous aqueous composition or uniform oil in water emulsion, and (v) once cooled, adding the tanning agent (e.g., the reducing sugar) to the homogenous aqueous composition or uniform oil in water emulsion, with optional agitation under condition similar to above, thereby forming the topical skincare composition. When present, the thickening agent may be added during step (i) or after step (iii) and before the addition of the tanning agent (i.e., before step (v)). Once cooled, the resulting topical skincare composition may then be filled into a desired packaging. The agitation may be provided by a propeller, such as a high shear mixer, and a high speed dissolver.

Method for Self-Tanning

The present disclosure provides methods of adjusting a color of the skin by topically applying the topical skincare composition, in one or more embodiments, onto the skin of a subject.

In order to achieve an acceptable degree of coloration or tan, a person who desires such coloration or tan can apply evenly an effective amount of the topical skincare composition over a desired body surface area for an effective application time. Thus, the topical skincare composition can be applied to provide subtle changes in skin color or more dramatic tanning effects. Further, the method disclosed herein may produce a rich, deep, aesthetically pleasing, and long lasting tan on the skin by simultaneously modifying hue angle, as well as increasing saturation and darkness of the skin color.

The topical skincare composition can be topically applied to wet or dye skin. Preferably, the desired area of skin is cleaned, and/or exfoliated prior to application. During the application, the topical skincare composition may be directly spread on an outer skin using, e.g., the hands, an applicator such as a wipe, puff, roller, or spray. The topical skincare compositions may be used as a single treatment to color the skin or applied in a progressive manner so the skin tan becomes more intense on subsequent applications until a desired degree of coloration is reached.

The topical skincare composition may be applied to the desired area as needed, preferably 1 to 4 times daily, preferably 2 to 3 times daily. The application may be conducted for at least 1 day, preferably for at least 2 consecutive days, more preferably for at least 3 consecutive days, even more preferably for at least 4 consecutive days, and up to 14 consecutive days, preferably up to 7 consecutive days, more preferably up to 6 consecutive days, even more preferably up to 5 consecutive days. Alternatively, the application may be performed intermittently. Application times outside of these ranges may also be used to vary the degree of coloration, as desired.

The appearance of a color (e.g., the color of a skin) can be expressed in terms of its hue (color), lightness (brightness), and saturation (vividness). Hue is a major attribute of a color perception used for the denotation of "unique hues" (e.g., red, yellow, blue), which are considered completely different hues. Saturation (also called chroma or colorfulness) refers to the "purity" of a specific hue. A highly saturated hue has a vivid, intense color, while a less saturated hue appears more muted and dull. With no saturation at all, the hue becomes a shade of gray. Lightness represents the lightness or darkness of a color perception. For example, an image with a higher lightness value reflects a greater quantity of light.

Quantifications of these color attributes (hue, saturation, lightness) can be performed using various color models including CIE (International Commission on Illumination) L*a*b* (CIELAB) color space model, CIE L*C*h° (CIEHCL) color space model, CIE XYZ model, RGB color model, and the like.

Figure 9:
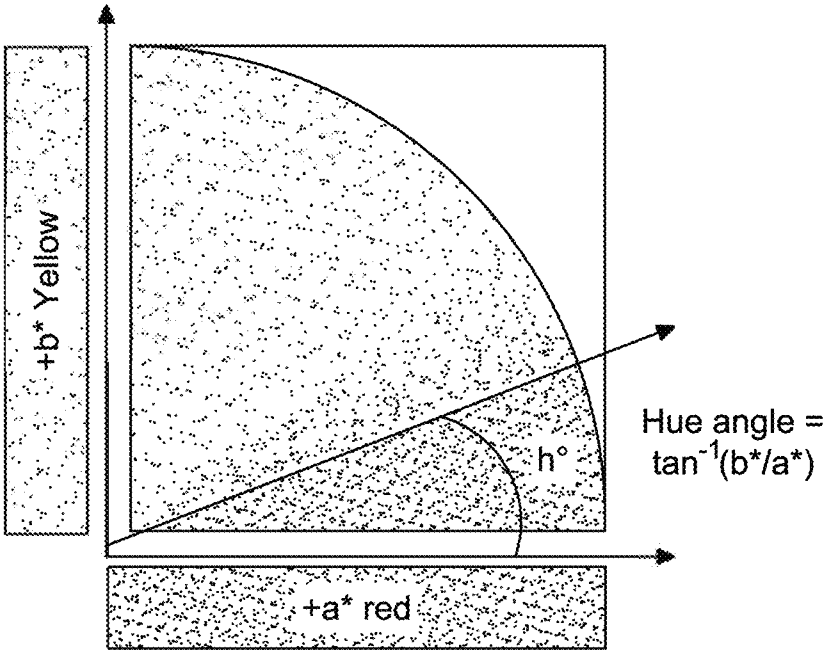
FIG. 9 is a portion of a chromaticity diagram portrayed by CIE L* C*h° and CIE L*a*b* color space models.

In some embodiments, the color of the skin herein is measured using the CIE L*a*b* model, where (i) L* denotes the lightness of the color which value runs from 0, representing black, to 100, representing white, (ii) a* denotes the red/green value of the color, and (iii) b* denotes the yellow/blue value of the color. In some embodiments, the color of the skin herein is measured using CIE L*C*h° model, where (i) L* denotes the lightness of the color and is the same as L* of the CIE L*a*b* model, (ii) C* denotes saturation (chroma) with value starts from 0, representing no saturation, and reaches 60, representing full saturation, and (iii) h° denotes hue angle. As shown in the chromaticity diagram (FIG. 9), the hue angle of the color of the skin herein is expressed in degrees and starts at the +a* axis. Specifically, a hue angle of 0° would be red (+a*), a hue angle of 90° would be yellow (+b*). The color attributes of the skin herein can be measured by a spectrophotometer, such as CM-700d, CM-2500d, or CM-2600d spectrophotometer manufactured by Konica Minolta.

The method herein may shift hue of the skin after application of the topical skincare composition. In some embodiments, the method herein reduces or increases hue angle h° of the color of the skin by at least about 0.1°, preferably at least about 0.2°, preferably at least about 0.3°, preferably at least about 0.4°, more preferably at least about 0.5°, even more preferably at least about 0.6°, yet even more preferably at least about 0.7°, and up to about 2°, preferably up to about 1.5°, preferably up to about 1.2°, more preferably up to about 1°, even more preferably up to about 0.8°, compared to that prior to the topical application.

Figure 5:
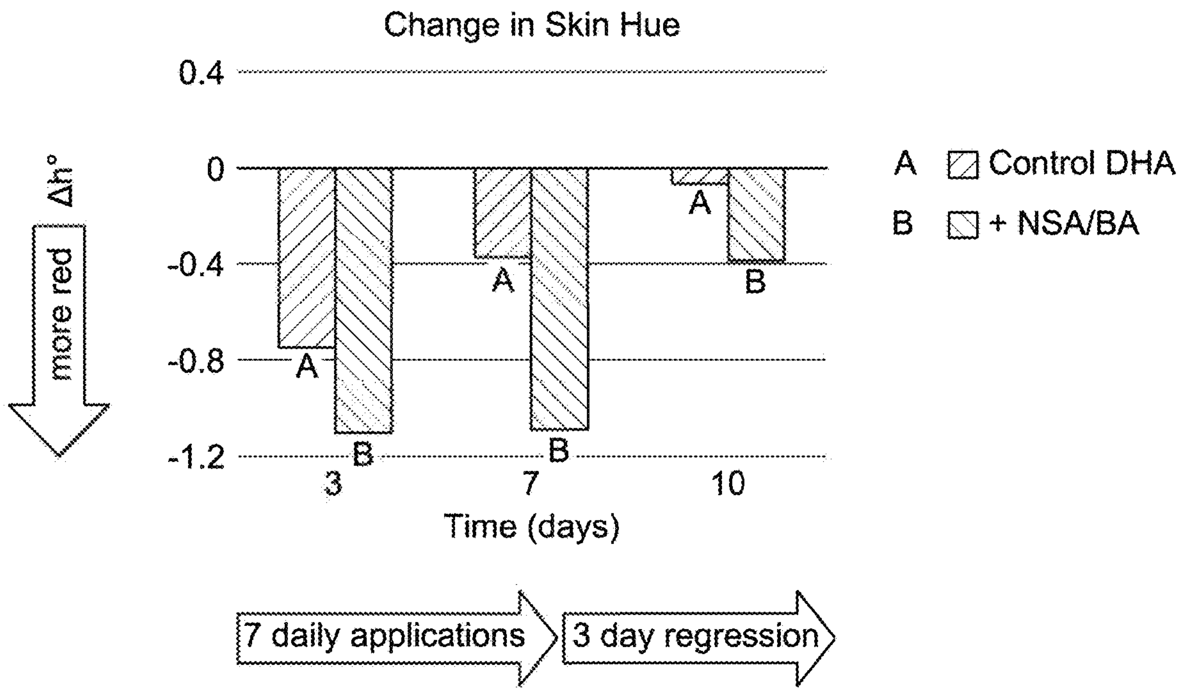
FIG. 5 is a bar graph showing changes in skin hue angle ($\Delta h°$) after 3 daily applications (1 application per day for 3 consecutive days), and 7 daily applications (1 application per day for 7 consecutive days) of a control composition ("A") having DHA alone, and a topical skincare composition ("B") containing DHA, NSA, and BA, respectively, as well as 3 days regression after the 7 daily applications.
Figure 6:
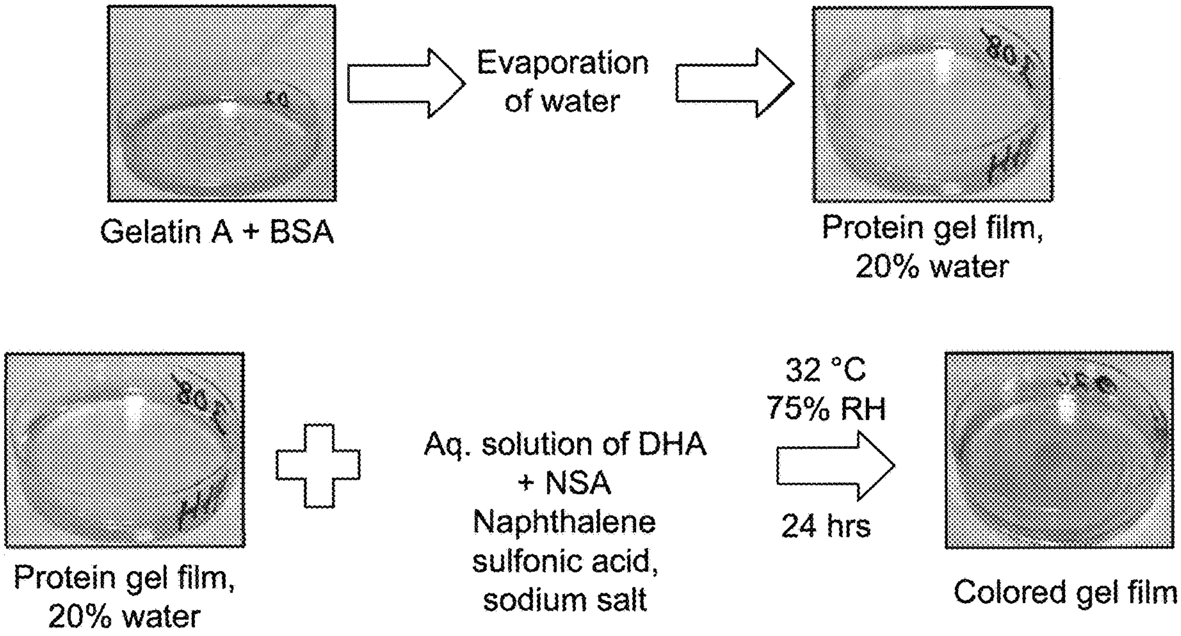
FIG. 6 is a schematic illustration showing the preparation of protein solid gel model study.

Preferably, the method herein reduces the hue angle h° of the color of the skin, for example by at least about 0.2°, preferably at least about 0.3°, preferably at least about 0.4°, more preferably at least about 0.5°, even more preferably at least about 0.6°, yet even more preferably at least about 0.7°, and up to about 1.5°, preferably up to about 1.2°, more preferably up to about 1°, even more preferably up to about 0.8°, compared to that prior to the topical application (see FIG. 5). A reduction in hue angle of the treated skin typically indicates that the topical skincare composition produces a bronze or red tone when applied to the skin.

The method herein may darken the color of the skin after application of the topical skincare composition. In some embodiments, the method herein reduces lightness L* of the color of the skin by at least about 1%, preferably at least about 2%, preferably at least about 3%, preferably at least about 4%, more preferably at least about 5%, even more preferably at least about 6%, yet even more preferably at least about 7%, and up to about 20%, preferably up to about 15%, preferably up to about 12%, more preferably up to about 10%, even more preferably up to about 8%, compared to that prior to the topical application.

In preferred embodiments, the method herein simultaneously changes the hue angle and reduces the lightness of the treated skin in accordance with the ranges specified above.

It is worth noting that the combination of a reducing sugar (A) (e.g., dihydroxyacetone, erythrulose), an aromatic sulfonate (B) (e.g., sodium 2-naphthalenesulfonate, sodium p-toluenesulfonate), and a carrier (C) (e.g., benzyl alcohol) provides unexpected tanning results (darker, longer lasting (i.e., more fade-resistant), more aesthetically pleasing coloration) compared to using only a reducing sugar.

Figure 4:
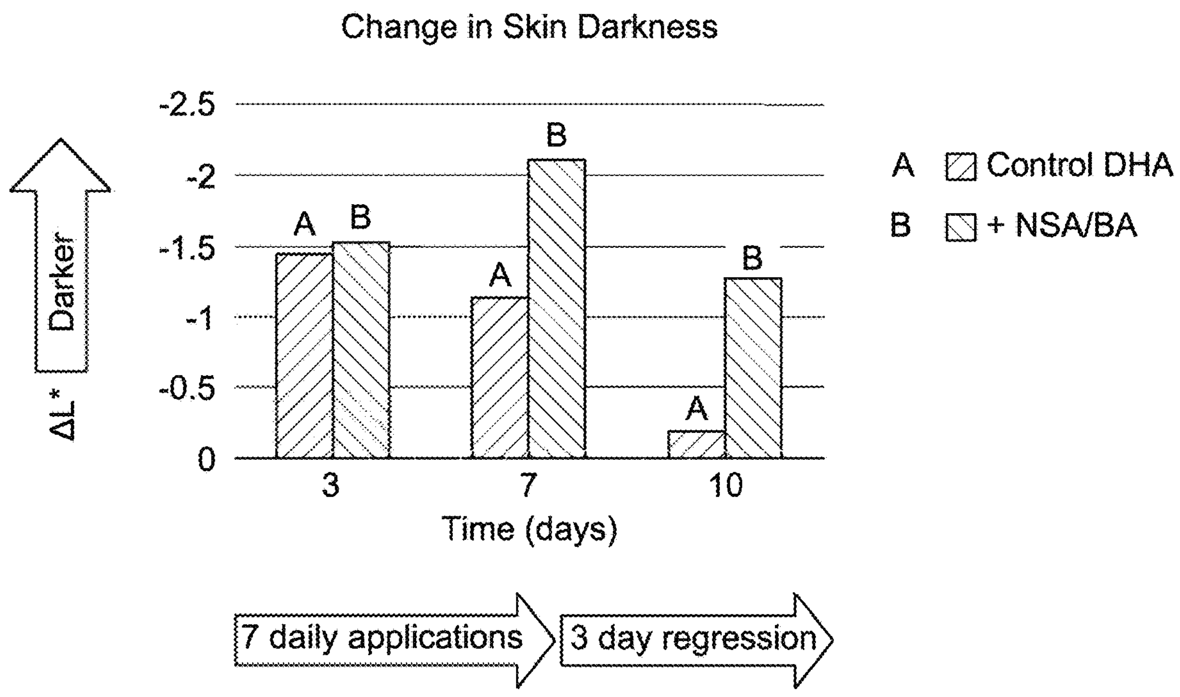
FIG. 4 is a bar graph showing changes in skin darkness ($\Delta L^*$) after 3 daily applications (1 application per day for 3 consecutive days), and 7 daily applications (1 application per day for 7 consecutive days) of a control composition ("A") having DHA alone, and a topical skincare composition ("B") containing DHA, NSA, and BA, respectively, as well as 3 days regression after the 7 daily applications.

For example, as shown in FIG. 5, using a reducing sugar alone does not significantly reduce the hue angle of the treated skin, and in some cases actually increases the hue angle after prolonged applications (e.g., after 7 days application). However, combining the aromatic sulfonate (B) and carrier (C) with the reducing sugar (A) significantly reduces the hue angle, thus imparting an aesthetically pleasing red/bronze tone to the treated skin. As shown in FIG. 4, using a reducing sugar alone leads to a reduction in skin lightness that is at least 30% less, preferably at least 35% less, more preferably at least 40% less, even more preferably 45% less, and up to 70% less, preferably up to 60% less, more preferably up to 50% less than using the combination of the reducing sugar (A), the aromatic sulfonate (B), and the carrier (C). Further, the artificial tan generated by this combination fades significantly slower than using a reducing sugar alone (e.g., less than about 40% color fade versus at least 80% color fade after 3 days regression).

The method herein may be utilized to adjust the color saturation of the skin. In some embodiments, the method herein increases saturation C* of the color of the treated skin by at least about 1%, preferably at least about 2%, preferably at least about 3%, preferably at least about 4%, more preferably at least about 5%, even more preferably at least about 6%, yet even more preferably at least about 7%, and up to about 20%, preferably up to about 15%, preferably up to about 12%, more preferably up to about 10%, even more preferably up to about 8%, compared to that prior to the topical application.

The examples below are intended to further illustrate the topical skincare compositions and are not intended to limit the scope of the claims.

EXAMPLES

Topical Skincare Compositions

Several example topical skincare compositions including comparative compositions used for tanning performance evaluations are given in Examples 1-3 below. The amount of each component is expressed in terms of weight percentage relative to a total weight of 100%. DHA refers to dihydroxyacetone, available from EMD Millipore. NSA refers to sodium 2-naphthalenesulfonate, available from Sugai Chemical. pTS refers to sodium p-toluenesulfonate. BA refers to benzyl alcohol, available from Kalama. 1,3-butylene glycol, methylparaben, ethylparaben, and SEPIPLUS™ S are each available from Oxea, Ueno, Sharon, and Seppic. PD refers to propanediol. GLY refers to glycerin. * denotes the example is a comparative example in the tables below.

Example 1

TABLE 1

Example topical skincare composition

| INCI Name | Amount (wt. %) |
|---|---|
| Water | 80.530 |
| 1,3-Butylene Glycol | 6.000 |
| Methylparaben | 0.300 |
| Ethylparaben | 0.150 |
| Benzyl Alcohol | 2.000 |
| Sodium Naphthalenesulfonate | 2.000 |
| SEPIPLUS ™ S (hydroxyethyl acrylate/sodium acryloyldimethyl taurate copolymer, polyisobutene, PEG-7 trimethylolpropane coconut ether) | 2.000 |
| Water | 5.000 |
| Dihydroxyacetone | 2.000 |
| Citric Acid (50%) | 0.020 |

INCI = International Nomenclature of Cosmetic Ingredients

TABLE 2

Example topical skincare composition for tanning evaluation (skin test)

| | Example 1* | Example 2 | Example 3* | Example 4 | Example 5 | Example 6* | Example 7 |
|---|---|---|---|---|---|---|---|
| DHA | 2 | 2 | 5 | 5 | 5 | 2 | 2 |
| Erythrulose | 0.5 | 0.5 | — | — | — | — | — |
| NSA | — | 2.5 | — | 2 | — | — | 3 |
| pTS | — | — | — | — | 2 | — | — |
| BA | — | 2.5 | — | — | — | — | 3 |
| Glycerin | 7 | 7 | — | — | — | 7 | — |
| Butylene Glycol | — | — | 6 | 6 | 6 | — | — |
| Propanediol | — | — | — | — | — | — | 7 |

TABLE 2-continued

| Example topical skincare composition for tanning evaluation (skin test) | | | | | | | |
|---|---|---|---|---|---|---|---|
| | Example 1* | Example 2 | Example 3* | Example 4 | Example 5 | Example 6* | Example 7 |
| Sepiplus S | 2.5 | 2.5 | — | — | — | — | — |
| Hydroxy-ethylcellulose | — | — | 1 | 1 | 1 | 1.25 | 1.25 |
| Xanthan Gum | — | — | — | — | — | 0.1 | 0.1 |
| Methylparaben | 0.2 | 0.2 | 0.3 | 0.3 | 0.3 | 0.3 | 0.3 |
| Ethylparaben | 0.1 | 0.1 | 0.15 | 0.15 | 0.15 | 0.15 | 0.15 |
| Cetearyl Alcohol | — | — | — | — | — | 3.5 | 3.5 |
| Mineral Oil | — | — | — | — | — | 1.75 | 1.75 |
| Petrolatum | — | — | — | — | — | 1.75 | 1.75 |
| Dimethicone | — | — | — | — | — | 1.5 | 1.5 |
| Ceteareth-20 | — | — | — | — | — | 1.2 | 12 |
| Octyldodecyl Myristate | — | — | — | — | — | 1 | 1 |
| Ethylhexyl Isononanoate | — | — | — | — | — | 1 | 1 |
| Steareth-2 | — | — | — | — | — | 0.6 | 0.6 |
| BHT | — | — | — | — | — | 0.1 | 0.1 |
| Fragrance | 0.5 | 0.5 | — | — | — | 0.5 | 0.5 |
| Phenoxyethanol | 0.15 | 0.15 | — | — | — | — | — |
| Citric Acid | 0.01 | 0.01 | 0.005 | 0.005 | 0.005 | 0.01 | 0.01 |
| Caramel | — | — | — | — | — | 0.04 | 0.04 |
| Water | q.s. | q.s. | q.s. | q.s. | q.s. | q.s. | q.s. |
| Total | 100.00 | 100.00 | 100.00 | 100.00 | 100.00 | 100.00 | 100.00 |

Figure 2:
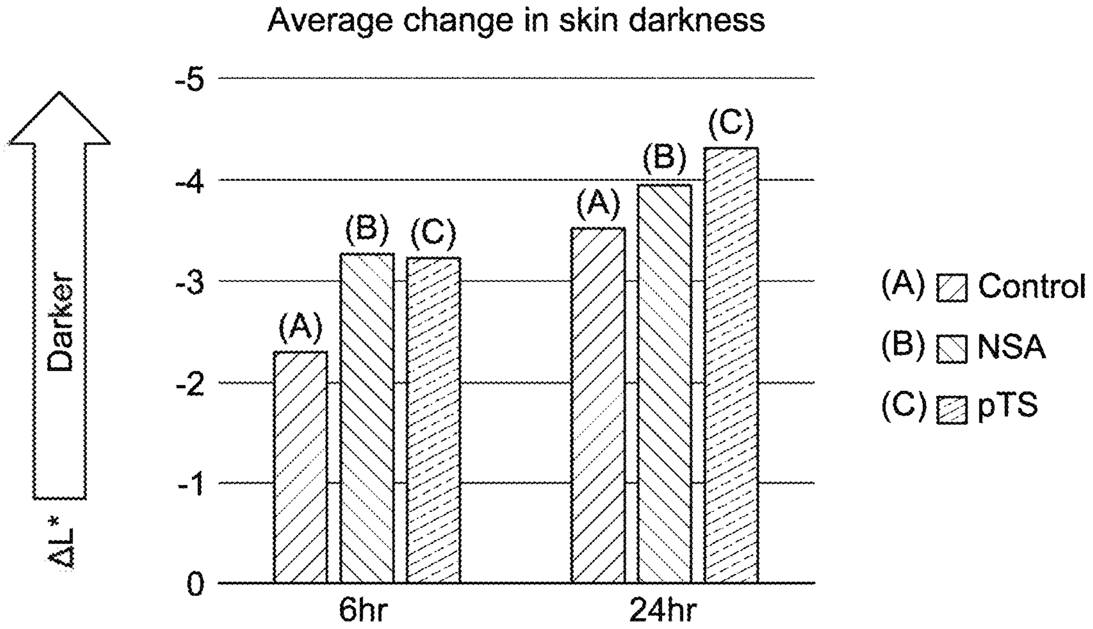
FIG. 2 is a bar graph illustrating changes in skin darkness 6 hours and 24 hours after applications of a control composition ("A") having DHA alone, a topical skincare composition ("B") containing DHA and NSA, and a topical skincare composition ("C") containing DHA and sodium p-toluenesulfonate (pTS), respectively.
Figure 3:
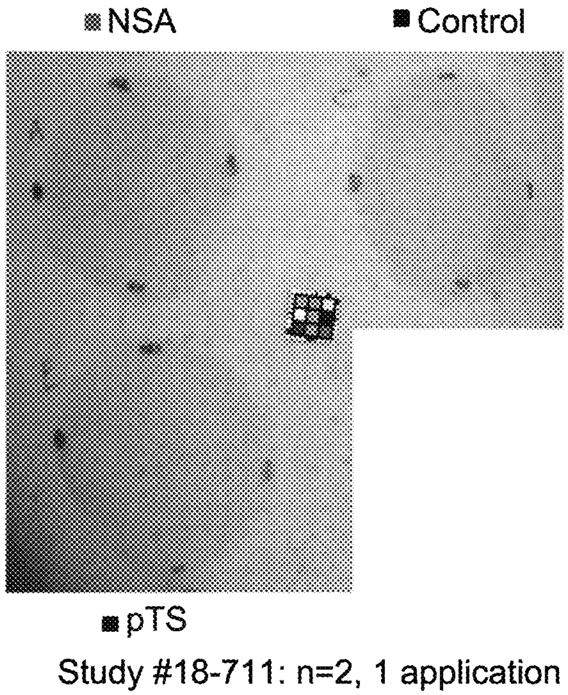
FIG. 3 is a color calibrated image showing human skin after treatment with a control composition having DHA alone ("control") (top right circle), after treatment with a topical skincare composition containing DHA and NSA ("NSA") (top left circle), and after treatment with a topical skincare composition containing DHA and pTS ("pTS") (bottom left circle), where color calibration was performed using the CASMATCH method (Bear Medic Co.).

Examples 1* and 2 are compositions "prototype" and "control", respectively tested in FIGS. 1A-1D; Examples 3*, 4, and 5 are compositions "Control", "NSA", and "pTS", respectively tested in FIGS. 2 and 3; and Examples 6* and 7 are compositions "Control DHA" and "+NSA/BA", respectively tested in FIGS. 4 and 5.

Example 2

Examples 1* and 2 are compositions "prototype" and "control", respectively tested in FIGS. 1A-1D; Examples 3*, 4, and 5 are compositions "Control", "NSA", and "pTS", respectively tested in FIGS. 2 and 3; and Examples 6* and 7 are compositions "Control DHA" and "+NSA/BA", respectively tested in FIGS. 4 and 5.

As shown in Table 1 and relevant figures, topical skincare compositions containing a reducing sugar (e.g., DHA, erythrulose) in combination with an aromatic sulfonate (e.g., NSA, pTS) (Examples 2, 4, 5, and 7) achieved remarkable tanning results in terms of darkness (more effective darkening), hue (more aesthetically pleasing red/bronze tone), and fade-resistance (longer lasting coloration) compared to using the reducing sugar alone (Comparative Examples 1*, 3*, and 6*).

TABLE 3

| Example topical skincare composition for tanning evaluation (protein solid gel model test) | | | | | | | |
|---|---|---|---|---|---|---|---|
| | Example 1* | Example 2 | Example 3 | Example 4 | Example 5 | Example 6 | Example 7 |
| DHA | 5 | 5 | 5 | 5 | 5 | 5 | 5 |
| NSA | — | 3 | — | 2 | 2 | 2 | 2 |
| pTS | — | — | 3 | — | — | — | — |
| Sodium cumene-sulfonate | — | — | — | — | — | — | — |
| Sodium polystyrene sulfonate | — | — | — | — | — | — | — |
| BA | — | 3 | — | 2 | 2 | 2 | 2 |
| PD | — | — | 3 | 10 | 7.5 | 5 | 2.5 |
| GLY | — | — | — | — | 2.5 | 5 | 7.5 |
| Citric Acid | 0.005 | 0.005 | 0.005 | 0.002 | 0.002 | 0.002 | 0.002 |
| Acetic Acid | — | — | — | — | — | — | — |
| Sodium Acetate | — | — | — | — | — | — | — |
| Water | q.s. | q.s. | q.s. | q.s. | q.s. | q.s. | q.s. |
| Total | 100.00 | 100.00 | 100.00 | 100.00 | 100.00 | 100.00 | 100.00 |

| | Example 8 | Example 9 | Example 10 | Example 11 | Example 12 |
|---|---|---|---|---|---|
| DHA | 5 | 5 | 5 | 5 | 5 |
| NSA | — | 2 | — | — | — |
| pTS | — | — | 2 | — | — |

TABLE 3-continued

| Example topical skincare composition for tanning evaluation (protein solid gel model test) | | | | | |
|---|---|---|---|---|---|
| Sodium cumene-sulfonate | — | — | — | 2 | — |
| Sodium polystyrene sulfonate | — | — | — | — | 2 |
| BA | — | — | — | — | — |
| PD | — | — | — | — | — |
| GLY | — | — | — | — | — |
| Citric Acid | — | — | — | — | — |
| Acetic Acid | 0.087 | 0.087 | 0.087 | 0.087 | 0.087 |
| Sodium Acetate | 0.701 | 0.701 | 0.701 | 0.701 | 0.701 |
| Water | q.s. | q.s. | q.s. | q.s. | q.s. |
| Total | 100.00 | 100.00 | 100.00 | 100.00 | 100.00 |

Figure 7A:
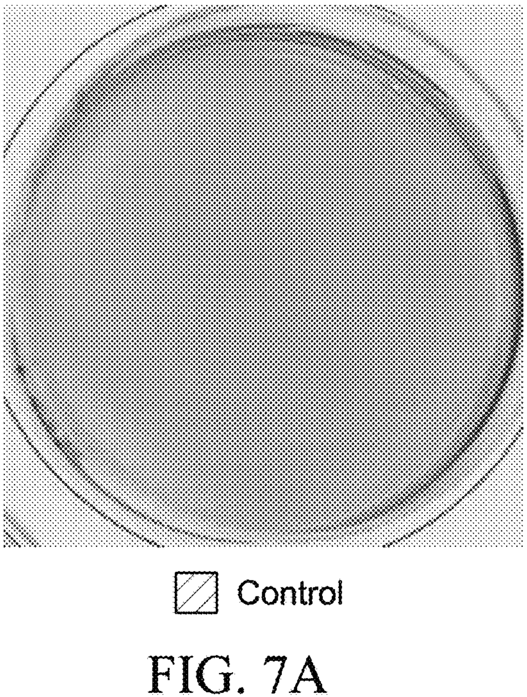
FIG. 7A is a picture showing a protein solid gel after treatment with DHA alone.
Figure 7B:
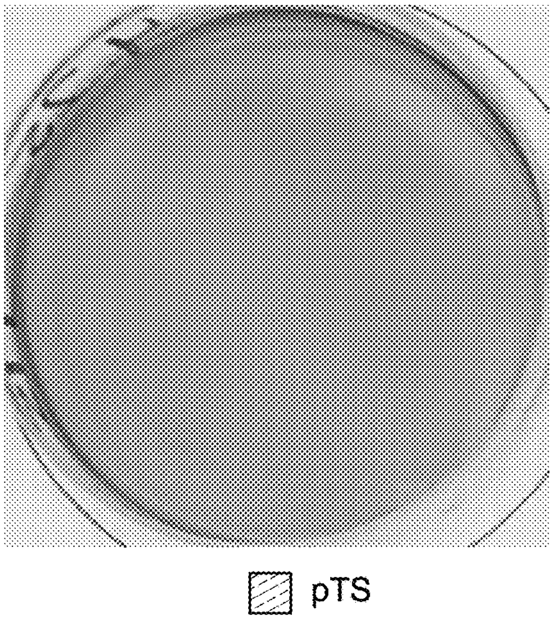
FIG. 7B is a picture showing a protein solid gel 24 hours after treatment with a mixture of DHA and pTS.
Figure 7C:
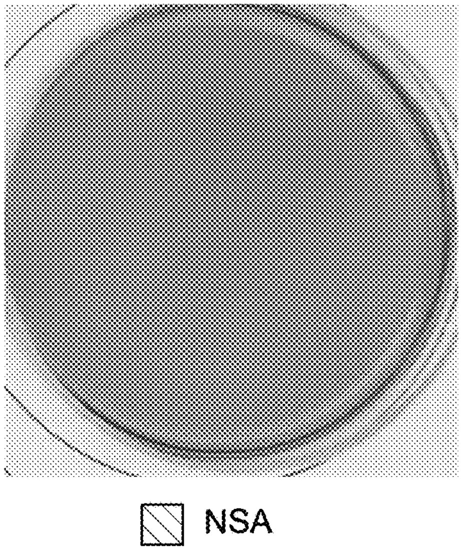
FIG. 7C is a picture showing a protein solid gel 24 hours after treatment with a mixture of DHA and NSA.
Figure 7D:
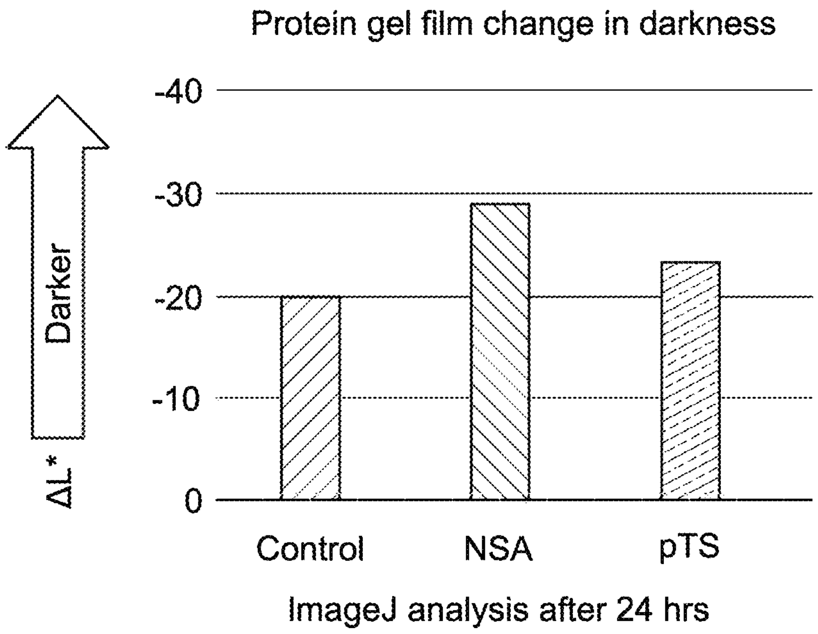
FIG. 7D is a bra graph showing changes in darkness of protein solid gel 24 hours after treatments with DHA alone ("control"), a mixture of DHA and NSA ("NSA"), and a mixture of DHA and pTS ("pTS"), respectively.
Figure 8A:
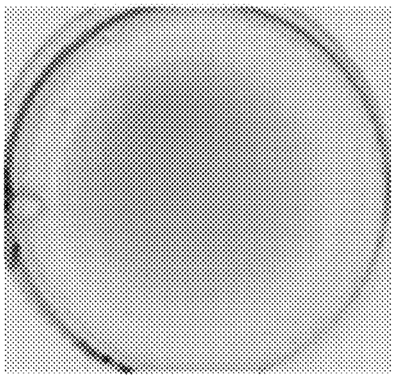
FIG. 8A is a picture showing a protein solid gel 7 hours after application of DHA alone at a temperature of 40° C. and pH of 5.4.
Figure 8B:
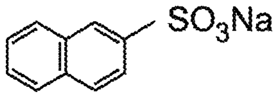
FIG. 8B is a picture showing a protein solid gel 7 hours after application of a mixture of DHA and NSA at a temperature of 40° C. and pH of 5.4.
Figure 8B:
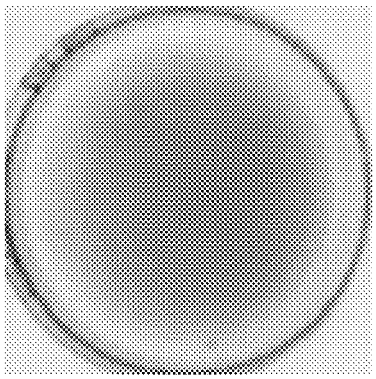
Figure 8C:
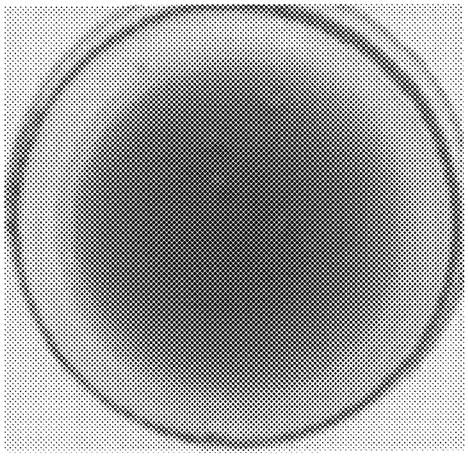
FIG. 8C is a picture showing a protein solid gel 7 hours after application of a mixture of DHA and pTS at a temperature of 40° C. and pH of 5.4.
Figure 8C:
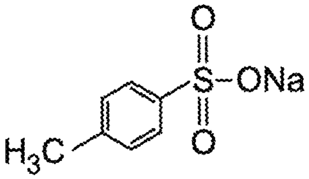
Figure 8D:
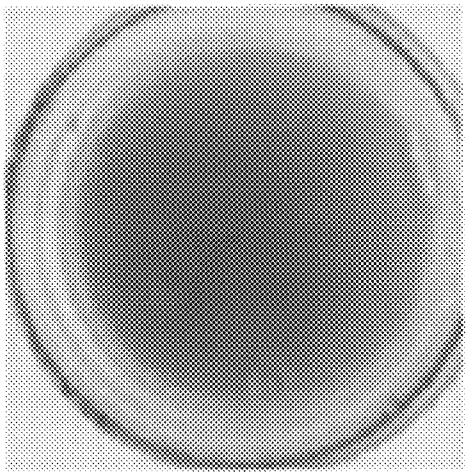
FIG. 8D is a picture showing a protein solid gel 7 hours after application of a mixture of DHA and sodium 4-isopropylbenzene sulfonate at a temperature of 40° C. and pH of 5.4.
Figure 8D:
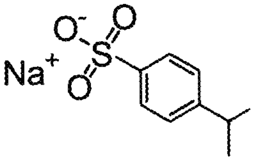
Figure 8E:
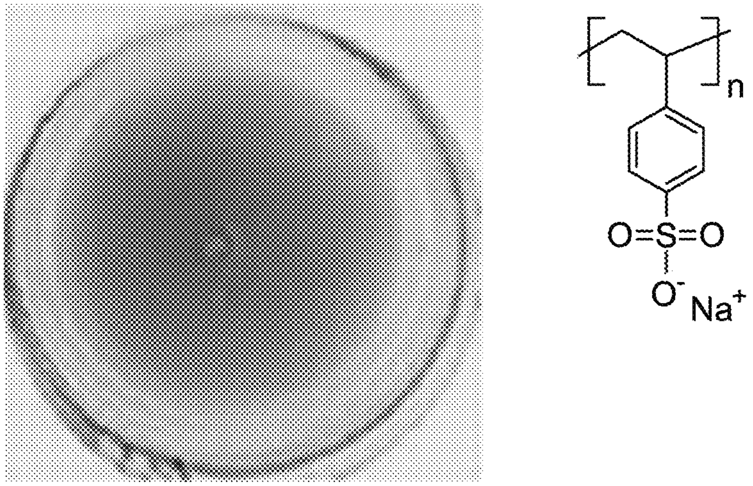
FIG. 8E is a picture showing a protein solid gel 7 hours after application of a mixture of DHA and poly(sodium 4-styrenesulfonate) at a temperature of 40° C. and pH of 5.4.

Examples 1*, 2, ad 3 are compositions "Control", "pTS", and "NSA", respectively tested in FIGS. 7A, 7B, and 7C; Examples 4, 5, 6 and 7 are compositions each containing: DHA, NSA, BA, and 1,3 propanediol (PD) at a weight ratio of 2:2:10 (Example 4), DHA, NSA, PD, and glycerin (Gly) at a weight ratio of 2:2:7.5:2.5 (Example 5), DHA, NSA, PD, and Gly at a weight ratio of 2:2:5:5 (Example 6), and DHA, NSA, PD, and Gly at a weight ratio of 2:2:2.5:7.5 (Example 7), respectively; and Examples 8*, 9, 10, 11, and 12 are compositions "DHA", "DHA/NSA", "DHA/Na p-toluenesulfonate", "DHA/Na Cumensesulfonate", and "DHA/Na Polystyrene sulfonate", respectively tested in FIGS. 8A-E.

Example 3

Examples 1*, 2, and 3 are compositions "Control", "pTS", and "NSA", respectively tested in FIGS. 7A, 7B, and 7C; Examples 4, 5, 6, and 1 are compositions each containing: DHA, NSA, BA, and 1,3-propanediol (PD) at a weight ratio of 2:2:5:5 (Example 4), DHA, NSA, PD, and glycerin (Gly) at a weight ratio of 2:2:7.5:2.5 (Example 5), DHA, NSA, PD, and Gly at a weight ratio of 2:2:5:5 (Example 6), and DHA, NSA, PD, and Gly at a weight ratio of: 2:2:2:5:7:5 (Example 7), respectively; and Examples 8*, 9, 101, 11, and 12 are compositions "DHA", "DHA/NSA", "DHA/Na p-toluenesulfonate", "DHA/Na Cumenesulfonate", and "DHA/Na Polystyrene sulfonate", respectively tested in Figs.

Preparation Methods

An exemplary process for preparing the example topical skincare composition is as follows:

Part A: Deionized water and 1,3-butylene glycol were first added to a main vessel and mixed thoroughly. The main vessel was heated to a temperature of 75-81° C. When the temperature of the vessel reached 75° C., parabens, BA, and NSA were added to the main vessel and mixed until clear. The heat was then turned off. SEPIPLUS™ S was added to the main vessel and mixed for about 20 minutes. Increasing agitation could be optionally applied as the mixture thickened after addition of SEPIPLUS™ S. The main vessel was cooled to a temperature of below 40° C., thereby forming the Part A.

Part B: Deionized water and DHA were added to a separate vessel and mixed until clear to form the Part B.

After Part A was cooled to a temperature below 40° C., part B was added to Part A to form part AB, which was mixed for about 5 minutes.

Finally, citric acid was added to part AB to adjust the pH to 3.5-4.0, thereby forming the topical skincare compositions.

Topical Skincare Composition Evaluation Methods (1) Skin Test

The example composition was applied to the skin in an amount of 2 $mg/cm^2$. The color parameters of the skin (e.g., lightness L*, hue angle h°) were measured before the application, and at various time points after the test product application specified in each test, followed by calculating the changes of each parameter (ΔL*, Δh°) compared to that before the application. Specifically, CM-2600d manufactured by Konica Minolta, Inc. was used as a colorimeter.

The skin tests could be performed as a consumer home-use study. For example, the data of FIGS. 4 and 5 were collected by the following method. Consumers applied one lotion product containing DHA alone ("Control DHA"), or DHA, NSA, and BA ("+NSA/BA"), to their arms and legs once daily for 7 days. Color measurements were taken on the arms and legs at baseline (Day 0), Day 3, and Day 7. Starting on Day 7, the panelists stopped using the test product. Additional color measurements on the arms and legs were taken on Day 10.

(2) Protein Solid Gel Model Test

Protein Solid Gel Sample Preparation:

Equipment: a digital balance (accurate to 0.01 g), a 600 mL beaker, three 300 mL beakers, a large water bath, two stainless steel insulators to fit 300 mL beakers, two micro-spatulas or tongue depressors, thirty six Falcon petri dishes with lids, and transfer pipettes.

Raw Materials: deionized water (DI water), Gelatin A (Gel A) stored on the bench at room temperature), and Bovine Serum Albumin (BSA) (stored at 5° C. in a laboratory refrigerator).

Preparation of Gelatin a Premix:

(i) obtained tare weight of 600 mL beaker+micro-spatula/tongue depressor;
(ii) added 40 g Gel A to the beaker;
(iii) added DI water to the beaker to make up to 200 g total solution;
(iv) placed the beaker with the solution into a water bath;
(v) set the temperature of the water bath to 60° C.;
(vi) used micro-spatula/tongue depressor to slowly mix the solution in the beaker frequently to prevent film formation on the top surface of the solution;
(vii) mixed the solution until homogeneous, which might take 1 hour.

Preparation of BSA Premix:

(i) obtained tare weight of 300 mL beaker+micro-spatula/tongue depressor;
(ii) added 8 g BSA to the beaker;
(iii) added DI water to the beaker to make up to 200 g total solution;

(iv) used micro-spatula/tongue depressor to slowly mix the solution;

(v) mix the solution until homogeneous, which might take 1 hour (no heat was added because BSA can degrade at higher temperatures); and (vi) placed the two remaining empty 300 mL beakers in stainless steel insulators and place them in the water bath. Weight bars could be used to hold the beakers down, if necessary;

Preparation of Petri Dishes:

(i) measured the weights of each dish without lid and recorded the value on the side of the dish;

(ii) arranged the dishes in order of increasing weight;

(iii) labeled the side of each dish with a common letter for the set and increasing whole numbers, e.g., Y01, Y02, Y03 . . . . Y10, Y11, etc.

Combination of the Premixes:

(i) once both Gel A and BSA premix solutions became clear and absent of aeration (each premixed with DI Water to obtain 200 g total solutions, see above), the Gel A and BSA premixes were each agitated for 2-3 minutes;

(ii) the BSA premix was added to the Gel A premix by slowly pouring the BSA premix down the interior perimeter of the beaker containing the Gel A premix, thereby forming a combined protein solution;

(iii) the combined protein solution was mixed slowly for 2 minutes;

(iv) removed the insulators from the water bath and dry the outside of the two 300 mL beakers (described in Section E, Step (vi)) with a towel; and (v) added the combined protein solution to the two insulated 300 mL beakers, by slowly pouring equal amount of the solution down the interior perimeter of each beaker.

Preparation of Gel Plates:

a desired amount of the combined protein solution was added to petri dishes using a transfer pipette. The dish containing the solution was then dried on a bench to form the gel plates.

Color Measurement of Protein Solid Gel:

The color measurement was performed using Image analysis provided by software ImageJ.

The present disclosure also contemplates other embodiments "comprising", "consisting of" and "consisting essentially of", the embodiments or elements presented herein, whether explicitly set forth or not.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A topical skincare composition, comprising:

(A) about 0.1 to 30 wt. % of a reducing sugar relative to a total weight of the topical skincare composition;

(B) an alkali metal aromatic sulfonate salt;

(C) a carrier comprising an aromatic alcohol; and (D) an organic solvent comprising a polyol, wherein the alkali metal aromatic sulfonate salt (B) has a topological polar surface area (tPSA) of less than 100 $Å^2$, a weight ratio of the alkali metal aromatic sulfonate salt (B) to the reducing sugar (A) (B):(A)) is 1:20 to 20:1, and a weight ratio of the carrier (C) to the organic solvent (D) ((C):(D)) is 1:20 to 1:2.

2. The topical skincare composition of claim 1, wherein the alkali metal aromatic sulfonate salt (B) is an optionally substituted phenyl sulfonate, an optionally substituted naphthyl sulfonate, or both.

3. The topical skincare composition of claim 1, wherein the alkali metal aromatic sulfonate salt (B) is sodium 2-naphthalenesulfonate.

4. The topical skincare composition of claim 1, wherein the alkali metal aromatic sulfonate salt (B) is sodium cumenesulfonate.

5. The topical skincare composition of claim 1, wherein the reducing sugar (A) is dihydroxyacetone, erythrulose, or both.

6. The topical skincare composition of claim 1, wherein the aromatic alcohol comprises benzyl alcohol.

7. The topical skincare composition of claim 1, wherein a weight ratio of the alkali metal aromatic sulfonate salt (B) to the carrier (C) ((B):(C)) is 1:4 to 4:1.

8. The topical skincare composition of claim 1, which is substantially free of a cationic copolymer.

9. A method of adjusting a color of the skin of a subject, the method comprising:

topically applying the topical skincare composition of claim 1 onto the skin of the subject, wherein the topical application reduces or increases a hue angle h° of the color by at least 0.5° compared to that prior to the topical application.

10. A method of adjusting a color of the skin of a subject, the method comprising:

topically applying the topical skincare composition of claim 1 onto the skin of the subject, wherein the topical application reduces a lightness L* of the color by at least 10% and reduces or increases a hue angle h° of the color by at least 0.5°, each compared to those prior to the topical application.

11. A method of adjusting a color saturation of the skin of a subject, the method comprising:

topically applying the topical skincare composition of claim 1 onto the skin of the subject, wherein the topical application increases a saturation C* of the color by at least 10% compared to that prior to the topical application.

12. A collection of topical skincare products for retail sale, the collection comprising:

(a) a first topical skincare composition that comprises:

(A) about 0.1 to 30 wt. % of a reducing sugar relative to a total weight of the topical skincare composition;

(B) an alkali metal aromatic sulfonate salt;

(C) a carrier comprising an aromatic alcohol; and (D) an organic solvent comprising a polyol, wherein the alkali metal aromatic sulfonate salt (B) has a topological polar surface area (tPSA) of less than 100 $Å^2$, and wherein a weight ratio of the alkali metal aromatic sulfonate salt (B) to the reducing sugar (A) ((B):(A)) is 1:20 to 20:1, and a weight ratio of the carrier (C) to the organic solvent (D) ((C):(D)) is 1:20 to 1:2

(b) a second topical skincare composition that comprises:

(A) about 0.1 to 30 wt. % of a reducing sugar relative to a total weight of the topical skincare composition;

(B) an alkali metal aromatic sulfonate salt; and (C) a carrier, wherein the alkali metal aromatic sulfonate salt (B) has a topological polar surface area (tPSA) of less than 100 Å$^2$, and wherein a weight ratio of the alkali metal aromatic sulfonate salt (B) to the reducing sugar (A) ((B):(A)) is 1:20 to 20:1, and wherein a content of the reducing sugar (A) present in the first topical skincare composition (a) is less than that of the reducing sugar (A) present in the second skincare composition (b), and wherein the contents are each relative to total weights of the first and second topical skincare compositions.

13. The collection of claim 12, wherein the first topical skincare composition (a) and the second topical skincare composition (b) are separately packaged.

* * * * *